US010548322B2

(12) United States Patent
Dhingra et al.

(10) Patent No.: US 10,548,322 B2
(45) Date of Patent: Feb. 4, 2020

(54) CONTROL OF RIPENING AND SENESCENCE IN PRE-HARVEST AND POST-HARVEST PLANTS AND PLANT MATERIALS BY MANIPULATING ALTERNATIVE OXIDASE ACTIVITY

(71) Applicant: Washington State University, Pullman, WA (US)

(72) Inventors: Amit Dhingra, Pullman, WA (US); Christopher Hendrickson, Pullman, WA (US); Seanna Hewitt, Pullman, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 15/456,330

(22) Filed: Mar. 10, 2017

(65) Prior Publication Data
US 2017/0208813 A1 Jul. 27, 2017

Related U.S. Application Data

(63) Continuation-in-part of application No. 13/833,928, filed on Mar. 15, 2013, now Pat. No. 9,591,847.

(60) Provisional application No. 61/719,859, filed on Oct. 29, 2012.

(51) Int. Cl.
*A01N 3/00* (2006.01)
*A23B 7/154* (2006.01)
*A01N 59/02* (2006.01)

(52) U.S. Cl.
CPC ............... *A01N 59/02* (2013.01); *A01N 3/00* (2013.01); *A23B 7/154* (2013.01)

(58) Field of Classification Search
None
See application file for complete search history.

(56) References Cited

U.S. PATENT DOCUMENTS 5,972,840 A 10/1999 Mottram
2006/0135369 A1 6/2006 Beltran

FOREIGN PATENT DOCUMENTS

CN 102550652 A 7/2012
WO 2012/162335 A2 11/2012

OTHER PUBLICATIONS

Polidoros et al., 2009, Physiologia Plantarum 137: 342-353.*
Vanlerberghe, 2013, Int. J. Mol. Sci. 14: 6805-6847.*
Abdalnoor, 2010, MSc Thesis "Effect of 1-Methylcyclopropene (1-MCP) on Quality and Shelf-Life of Banana Fruits", University of Khartoum, pp. 1-103.*
Watkins, 2006, Biotechnology Advances 24: 389-409.*
Watkins, 2008, HortScience 43: 86-94.*
Pistelli et al., 1996, Plant Science 119: 23-29.*
Xu et al., 2012, Journal of Experimental Botany 63: 5705-5716.
Considine et al., 2001, Plant Physiology 126: 1619-1629.
Xiao et al., 2010, Zeitschrift fur Naturforschung. Section C, Biosciencs 65.7/8: 463-471.
Duque and Arrabaca, 1999, Physiologia Plantarum 107: 24-31.
Rhoads et al., The Plant Cell, Sep. 1992, pp. 1131-1139, vol. 4, American Society of Plant Physiologists.

* cited by examiner

*Primary Examiner* — Bratislav Stankovic
(74) *Attorney, Agent, or Firm* — Husch Blackwell LLP

(57) ABSTRACT

Methods of controlling the maturation of plants and/or plant products (e.g. fruit, vegetable, ornamentals, etc.) by manipulating Alternative Oxidase (AOX) activity. An increase in activity hastens the maturation process while a decrease in activity slows or stops maturation.

16 Claims, 14 Drawing Sheets

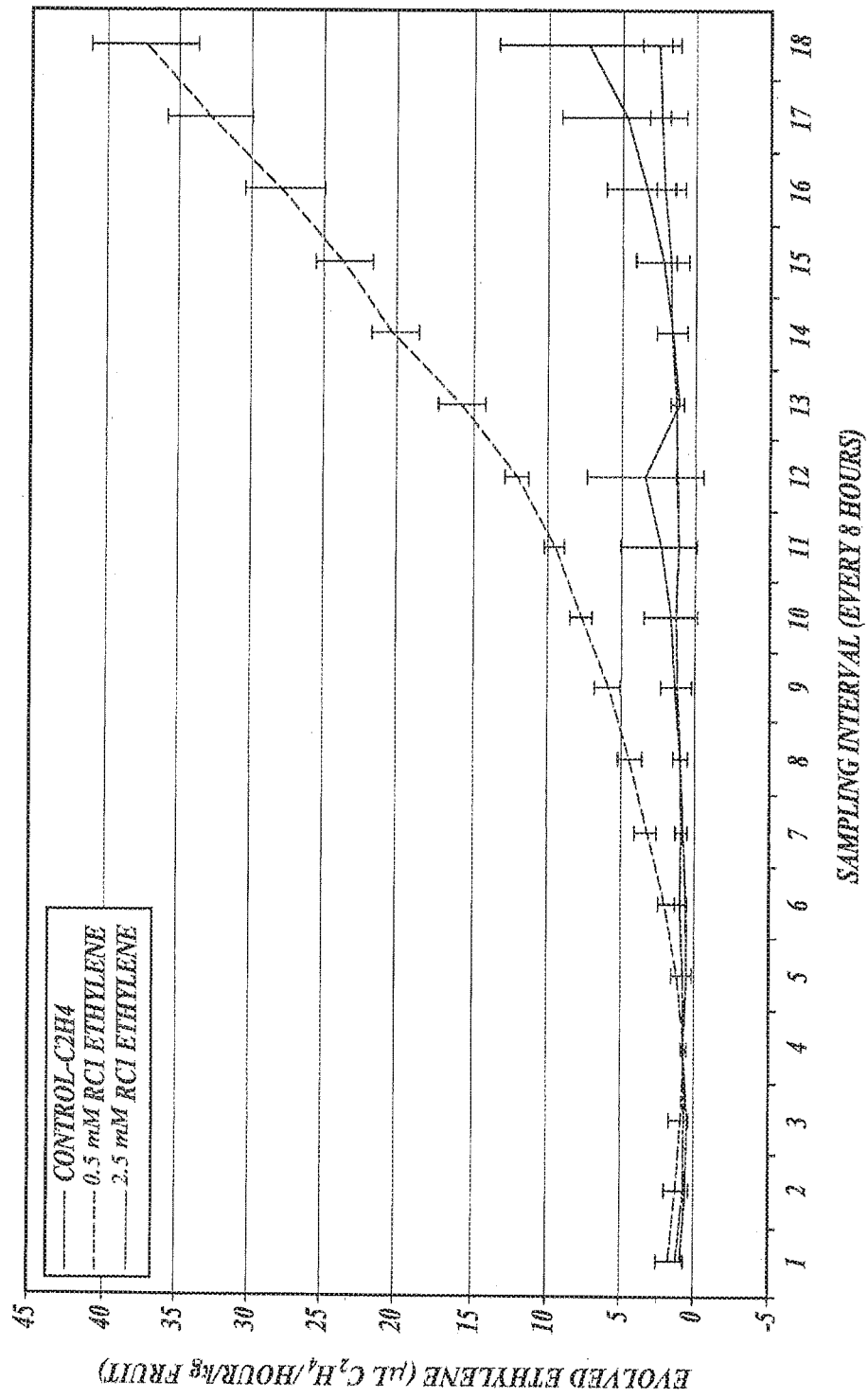

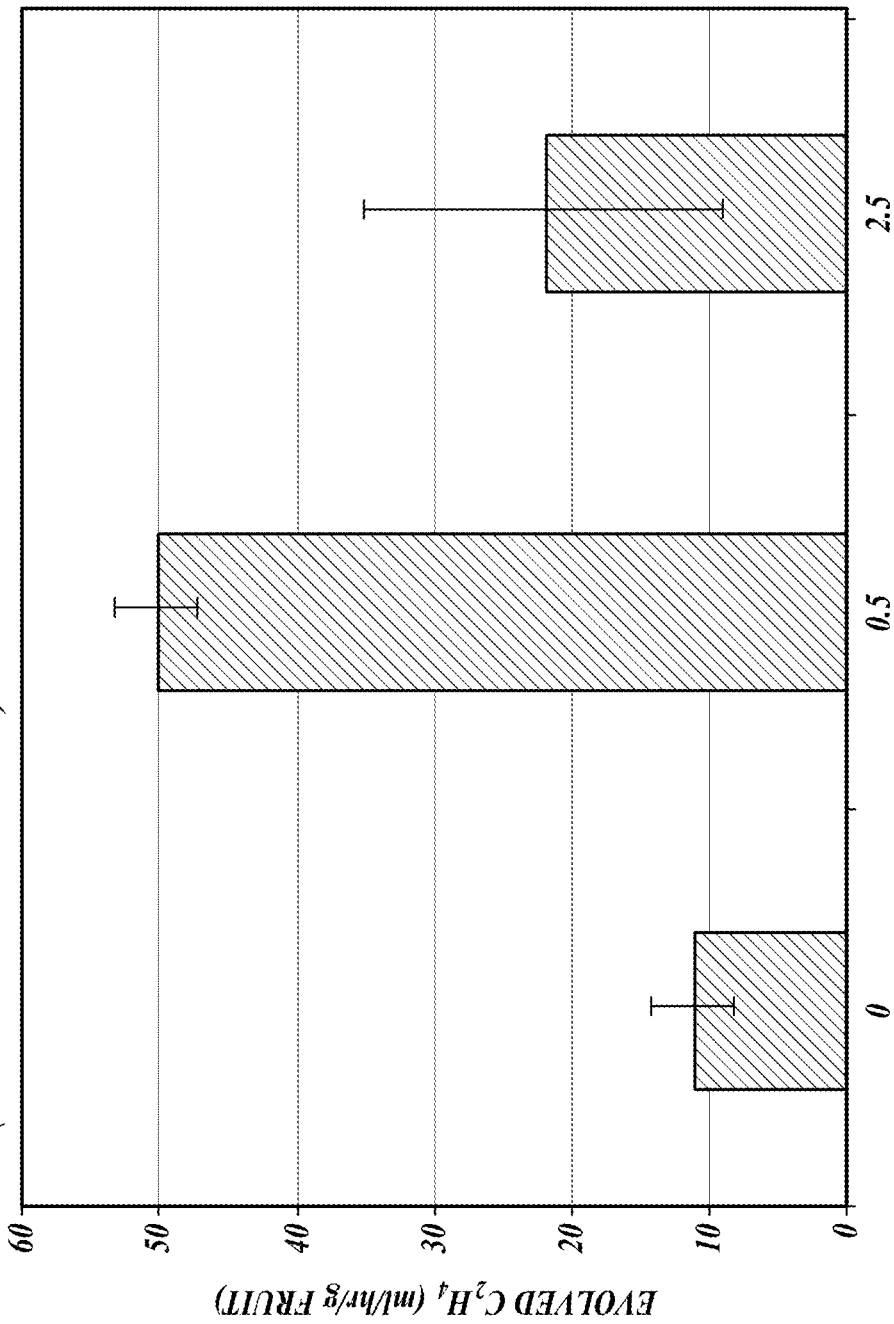

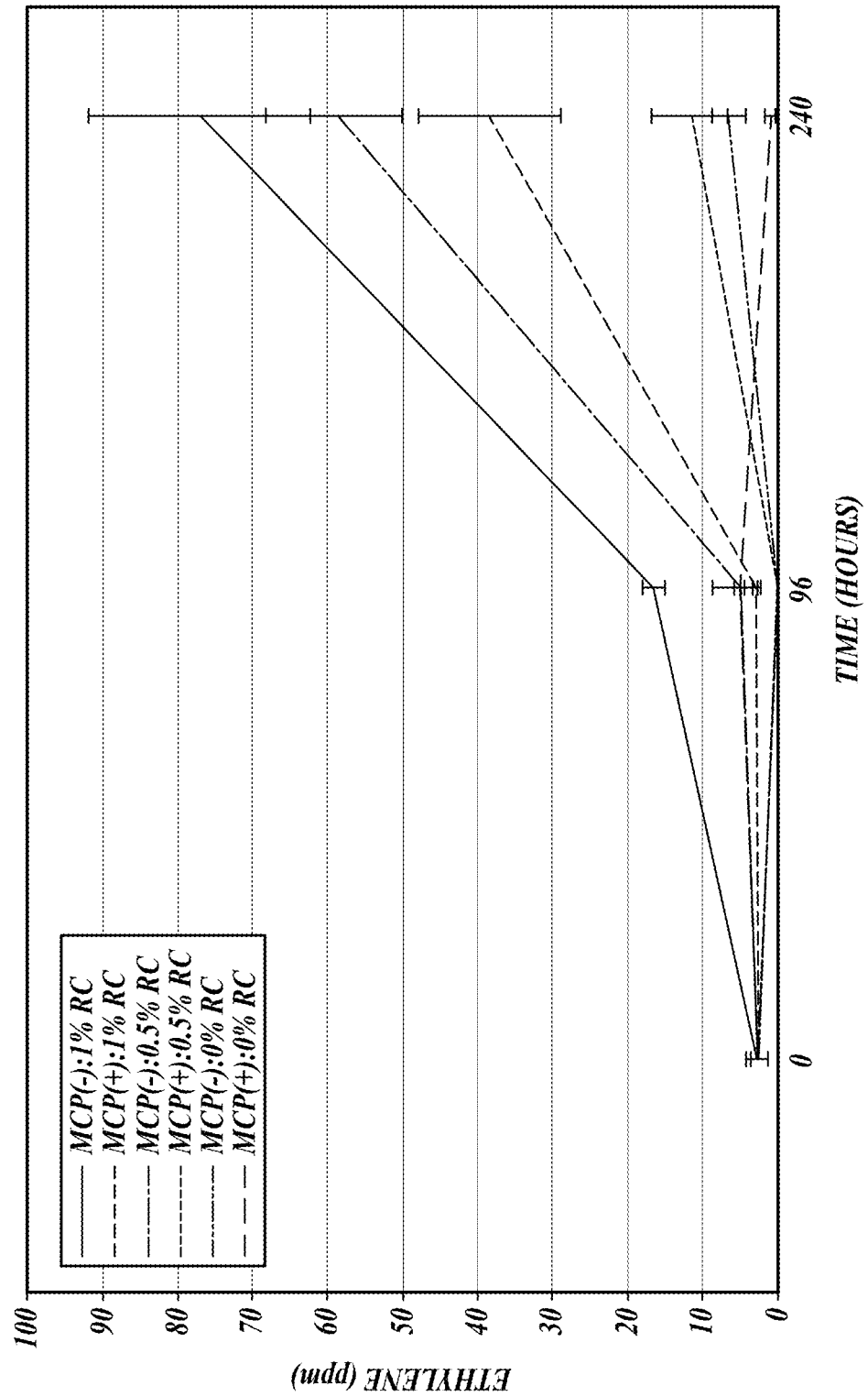

CONTROL OF RIPENING AND SENESCENCE IN PRE-HARVEST AND POST-HARVEST PLANTS AND PLANT MATERIALS BY MANIPULATING ALTERNATIVE OXIDASE ACTIVITY

CROSS-REFERENCES TO RELATED APPLICATIONS

This application is a continuation-in-part of U.S. patent application Ser. No. 13/833,928, filed Mar. 15, 2013, which claims the benefit of U.S. Provisional Application No. 61/719,859, filed Oct. 29, 2012, the disclosures of which are hereby expressly incorporated by reference in their entirety herein.

STATEMENT OF GOVERNMENT LICENSE RIGHTS

This invention was made with Government support under Grant No. USDA 2009-31100-06053 awarded by the United States Department of Agriculture. The Government has certain rights in the invention.

FIELD OF THE INVENTION

The invention generally relates to methods of controlling the maturation of plants and plant materials. In particular, the invention provides methods to inactivate and activate Alternative Oxidase (AOX) gene expression in order to control the rate and timing of the maturation (e.g. ripening, senescence, etc.) of plants/plant products such as fruit, vegetables, ornamental plants, and other produce.

BACKGROUND

Climacteric fruit and cut flowers are typically treated with chemicals such as 1-methylcyclopropene (1-MCP) to block or slow down ripening and to extend storage and shelf-life. 1-MCP binds ethylene receptors blocking all downstream physiological and metabolic processes. Primarily, sensing of ethylene and subsequent signaling are blocked. While the use of 1-MCP has produced somewhat desirable results for some produce, its use has distinct drawbacks. For example, apples treated with 1-MCP remain desirable in terms of appearance, but they produce no or very limited amounts of volatile compounds, which reduces the fruit quality and desirability to consumers. The use of 1-MCP in some other fruits has been outright detrimental. For example, pears treated with 1-MCP do not ripen despite treatment with exogenous ethylene or the use of protocols intended to condition the fruit to ripen (e.g. various cold temperature treatments).

It would be desirable to have available methods of treating plants and plant materials (e.g. fruit, vegetables, ornamentals, etc.) so that they can be stored and shipped in an immature state (e.g. without ripening), and then readily matured at a desired time or within a desired time frame. It would be a boon to have available a method or mechanism to induce maturation of stored produce in a manner that results in the development of characteristics (e.g. softness, odor, aromas etc.) of produce that is allowed to mature naturally.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The alternative pathway respiration-related Alternative Oxidase (AOX) gene expression coincides with climacteric peak which is the hallmark of climacteric fruit (Duque and Arrabaca, 1999; Xu et al, 2012). However, prior to the present invention, the role of the enzyme as a controlling factor in plant maturation was not known. Experiments described herein have now shown that AOX gene expression is responsible for the physiological changes in plants and plant products which occur during ripening and senescence. Accordingly, the present invention provides methods to impact or influence expression of the AOX gene in order to slow or stop these processes, and/or to begin or resume the processes in a controlled, predictable manner.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

In some aspects, the invention provides methods of storing and subsequently maturing a plant or plant product. The methods comprise the steps of i) inactivating one or more Alternative Oxidase (AOX) genes in said plant or plant product; and, subsequently, ii) exposing said plant or plant product to an agent that activates said one or more AOX genes. Activation of the one or more AOX genes results in the onset of maturation of the plant/plant product. The step of inactivating may be carried out chemically or physiologically. If carried out chemically, this may be done by exposing the plant or plant product to 1-methylcyclopropene (1-MCP) or glycine betaine The agent that is applied may be applied as a gas or as a liquid. The agent may be applied by drenching, by spraying or by a slow release method. The agent may be or be applied with an antimicrobial.

In some aspects, the step of inactivating is carried out physiologically by exposure to cold. In some aspects, the step of inactivating is carried out physiologically by exposure to a temperature less than room temperature and above freezing including but not limited to 65°-55° F., 55°-45° F., 45°-35° F., 34° F., or 33° F.

The agent that activates at least one AOX gene is, for example, hydrogen sulfide, glyoxylic acid, salicylic acid, pyruvate, hydroxypyruvate, or a mixture of alanine and 2-oxoglutarate. The one or more AOX genes include AOX1 and AOX 2 or additional AOX gene family members. The plant or plant product may be, for example, a fruit, a vegetable, a tuberous root, a taproot, a bulb, a corm, a rhizome or a tuber, with exemplary fruits being pears, apples, bananas, avocadoes, and mangos; and exemplary vegetables being tomatoes and peppers. In some aspects, one or both of the steps of inactivating and exposing are carried out pre-harvest. In other aspects, one or both of the steps of inactivating and exposing are carried out post-harvest. The invention also provides methods of overcoming blockage in ripening or senescence of a plant or plant product. The methods comprise a step of exposing the plant or plant product that has experienced a blockage in ripening or senescence to an agent that activates one or more Alternative Oxidase (AOX) genes. In some aspects, the agent is, for example, hydrogen sulfide, glyoxylic acid, salicylic acid, pyruvate, hydroxypyruvate, or a mixture of alanine and 2-oxoglutarate. The plant or plant product may be, for example, a fruit, a vegetable, a tuberous root, a taproot, a bulb, a corm, a rhizome or a tuber.

The invention also provides methods of hastening the maturation of an immature plant or plant product. The methods comprise a step of exposing the immature plant or plant product to an agent that activates one or more Alternative Oxidase (AOX) genes. In some aspects, the agent is, for example, hydrogen sulfide, glyoxylic acid, salicylic acid, pyruvate, hydroxypyruvate, or a mixture of alanine and 2-oxoglutarate. The plant or plant product may be, for example, a fruit, a vegetable, a tuberous root, a taproot, a bulb, a corm, a rhizome or a tuber.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 6A and 6B. Evolution of ethylene measured in microliter per hour per kilogram fruit in per fruit blocked for ripening by 1-MCP. A, effects of exposure to RC-1: ethylene evolution is observed 48 hrs post-treatment with RC-1; B, effects of exposure to of Ripening compound-2 (RC-2): at 0.25 mM of RC-2 ethylene evolution is observed within 16 hrs.

FIG. 10. Amount of ethylene evolved from 1-MCP pre-treated fruit after slicing and treating with 0.5 mM and 2.5 mM of glyoxylic acid.

FIGS. 11A and 11B. A, Sliced pear fruit packaged in modified atmosphere bags. B, Graphical representation of the amount of ethylene evolved from 1-MCP pre-treated fruit that was then sliced and treated with a range of concentrations of glyoxylic acid. Note that the fruit treated with some of the concentrations releases more ethylene than the control fruit.

FIG. 12. Internal ethylene measurements in 1-MCP and control fruit when treated with 0.5% and 1% glyoxylic acid. The status of 1-MCP pre-treatment and exposure to glyoxylic acid (on whole pears) is indicated for each assay. A one quarter slice of each pear was removed, sectioned into four pieces, and placed in a gas extraction chamber to assay ethylene production.

DETAILED DESCRIPTION

Figure 1:
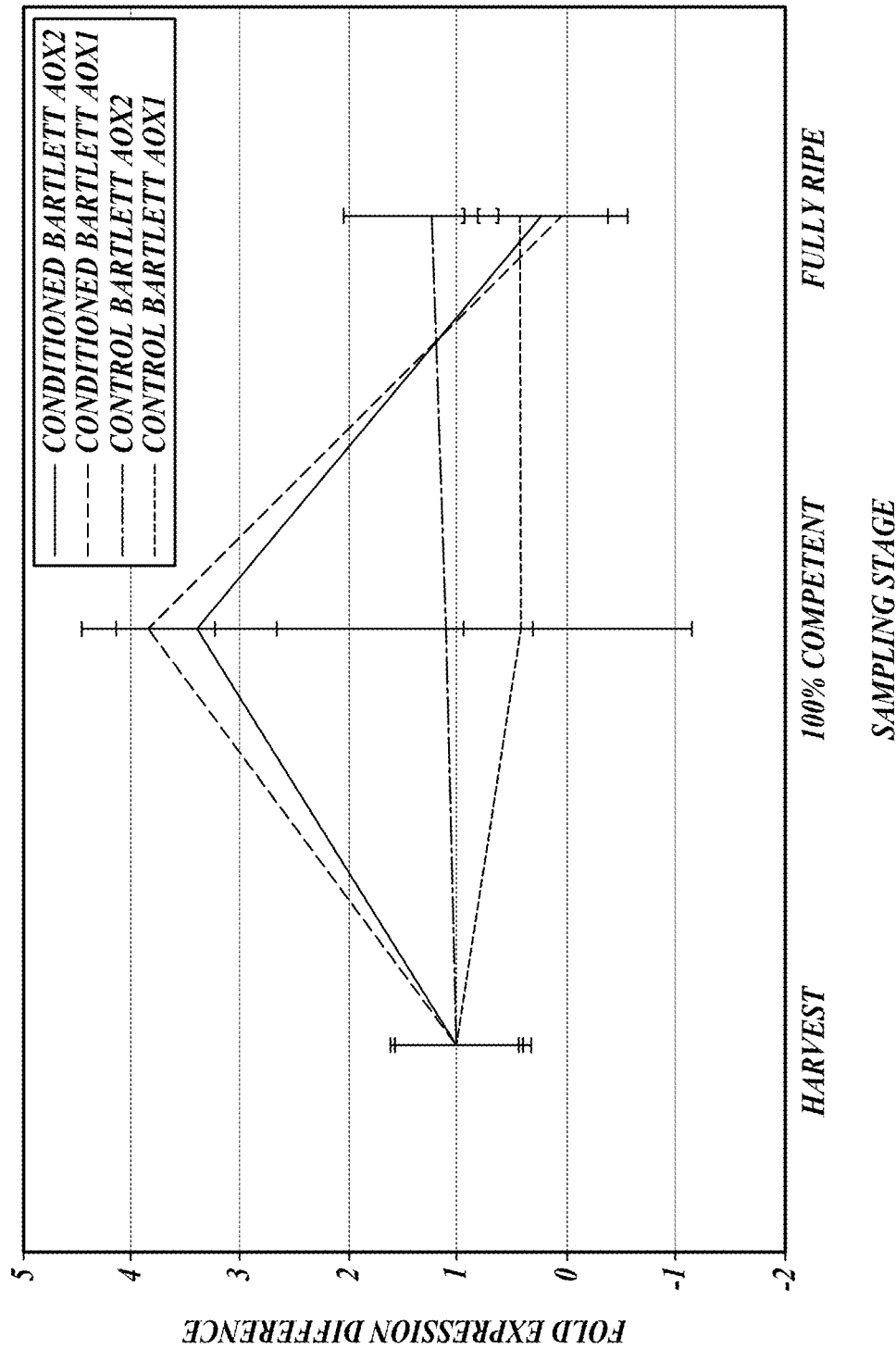
FIG. 1. Relative expression of alternative oxidase (PcAOX1, 2) expression in harvested, fully conditioned, and fully ripened pear fruit among 3 biological replicates. Ct-values were normalized to a control gene, 2-log transformed, then inverted. Error bars represent standard deviation. Compared to controls, AOX expression is 3 to 3.75 fold higher in conditioned fruit.

In some aspects, the present invention exploits previously unknown properties of AOX enzymes in order to control or "time" plant/plant product maturation in a pathway-specific manner. In some aspects, the invention provides methods to control plant/plant product maturation, the methods including a step of first deactivating AOX (e.g. to induce cessation of or prevent or block onset of physiological or developmental changes which are characteristic of and/or which lead to ripening, senescence, etc.), and then, after a desired period of time, activating AOX to commence or recommence physiological/developmental changes which are characteristic of and/or which lead to maturation. In other aspects, methods to control plant/plant product maturation include only a step of activating AOX. The methods may be used pre- or post-harvest and in a variety of scenarios, as described in detail below.

The following definitions apply throughout:

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, melt index, temperature etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

By "plants and/or plant products" or "plant materials" we mean photosynthetic, multicellular organisms of the kingdom Plantae including such groups as flowering plants, conifers, ferns and mosses; and/or products (e.g. reproductive and/or carbohydrate storage products) and parts thereof, e.g. leaves, blossoms, roots, stalks, stems, needles, fruit, seeds, buds, branches, bulbs, corms, rhizomes, and tubers. The "plants and/or plant products" may be pre-harvest (e.g.

still attached to a tree, bush, etc. or still in the ground, or may be post-harvest, e.g. detached from a tree or bush, or extirpated from the ground or cleaved, cut or otherwise removed from a stalk, stem, vine, etc. The plants may or may not have been subject to prior post-harvest treatment(s) to control ripening. The plants may be processed e.g. slices or wedges or other portions of the plant may be treated, as may be packaged plants/plant products, and mixtures of plants/plant products. The plants may be climacteric or non-climacteric. Climacteric is a botanical term that indicates the period during which a plant part inclusive of the ones listed above exhibit a rise in the rate of respiration and release of ethylene at the time of ripening or maturing. Non-climacteric or aclimacteric plants are those that ripen without an increase in rate of respiration or release of ethylene.

By "AOX" gene or protein, we mean an alternative pathway respiration-related Alternative Oxidase (AOX) gene/protein. AOX is an enzyme that forms part of the electron transport chain in plants, as well as some fungi, protists and possibly some animals. The alternative oxidase is an integral membrane protein that is tightly bound to the inner mitochondrial membrane and which provides an alternative route for electrons passing through the electron transport chain to reduce oxygen. Since several proton-pumping steps are bypassed in this alternative pathway, activation of the oxidase reduces ATP generation. Particular examples of AOX genes include *Pyrus communis* AOX 1 and AOX 2 (PcAOX1 and PcAOX2). As used herein, "AOX" may refer to one AOX gene or protein, or may refer collectively to more than one AOX gene or protein.

As used herein, an agent to activate at least one AOX gene refers to increased expression of the AOX gene or increased production of AOX protein, or increased translation of the AOX mRNA as compared to the expression of the AOX gene, or production of the AOX protein or translation of the AOX mRNA without the agent.

As used herein, an agent to activate at least one AOX gene can result in 2-5% or 5-10% or 10-15%, or 15-20%, or 20-25%, or 25-30%, or 30-35%, or 35-40%, or 40-45%, or 45-50%, or 50-55%, or 55-60%, or 60-65%, or 65-70%, or 70-75%, or 75-80%, or 80-85%, or 85-90%, or 90-95% increased expression of the AOX gene as compared to expression of the gene without the agent.

As used herein, an agent to activate at least one AOX gene can result in 2-5% or 5-10% or 10-15%, or 15-20%, or 20-25%, or 25-30%, or 30-35%, or 35-40%, or 40-45%, or 45-50%, or 50-55%, or 55-60%, or 60-65%, or 65-70%, or 70-75%, or 75-80%, or 80-85%, or 85-90%, or 90-95% increased production of the AOX protein as compared to production of the AOX protein without the agent.

As used herein, an agent to activate at least one AOX gene can result in 2-5% or 5-10% or 10-15%, or 15-20%, or 20-25%, or 25-30%, or 30-35%, or 35-40%, or 40-45%, or 45-50%, or 50-55%, or 55-60%, or 60-65%, or 65-70%, or 70-75%, or 75-80%, or 80-85%, or 85-90%, or 90-95% increased translation of the AOX mRNA as compared to translation of the AOX mRNA without the agent.

By "maturation" as used herein, we mean the onset of physiological processes which lead to senescence in a plant or in plant material. In some cases (e.g. fruit), ripening occurs as a result of these processes. Other typical changes include ethylene release, changes in pigment and hence color, increase in sugars, changes in respiration, changes in soluble solids content, changes in titratable acidity, changes in fruit firmness, development of abscission zones, breakdown of cellular membranes, changes in the content of aromatic compounds etc.

Climacteric stage: For some fruits, a hallmark of entering into the maturation process is the climacteric stage, a stage of fruit ripening associated with ethylene production and cell respiration rise. Apples, bananas, melons, apricots, tomatoes (among others) are climacteric fruit. Climacteric is the final physiological process that marks the end of fruit maturation and the beginning of fruit senescence. Its defining point is the sudden rise in respiration of the fruit and normally takes place without any external influences. After the climacteric period, respiration rates (noted by carbon dioxide production) return to or below the point before the event. The climacteric event also leads to other changes in the fruit including (but not limited to) pigment changes and sugar release, flesh softening, release of aroma and titratable acidity. For those fruits raised as food the climacteric event marks the peak of edible ripeness, with fruits having the best taste and texture for consumption. After the event fruits are more susceptible to fungal invasion and begin to degrade with cell death.

The invention thus provides methods of inducing plants and/or plant products to exit or leave a state of active maturation, and/or to enter or re-enter a state of active maturation. In one embodiment, the plants/plant products are undergoing a maturation process and, according to methods of the invention, human intervention interrupts this process by inactivating AOX. The means of inactivating AOX may be, for example, imposing an environmental condition on the plant/plant product, or exposing the plant/plant product to (e.g. applying) an agent which has the effect of arresting maturation. Plants/plant products may thus be caused to remain in an immature, unripened state by any of several artificial (i.e. non-natural) means, including those which involve the manipulation of environmental conditions, and/or exposure of the plants/plant products to an agent which delays maturation, etc. Examples of the artificial manipulation of environmental conditions include but are not limited to: exposing the plants/plant products to cold, e.g. storing them at a temperature of less than about 15, 10, 5, 0, or −0.5° C.; preventing exposure to light, storage in modified atmospheres containing reduced amounts of respiration substrate, reduced amount of oxygen, increased amounts of nitrogen etc. Examples of agents that can be used to prevent or delay maturation include but are not limited to: 1-MCP (1-methylcyclopropene), AVG (aminoethoxyvinylglycine), and cytokinins (such as but not limited to zeatin, isopentyladenine, etc.). In addition, combinations of these may be used, e.g. plants/plant products may be stored in the cold and/or in the presence of one or more of such agents.

The plants/plant products in which an absence or decrease in AOX has been initiated (e.g. decreased below levels which would be present if measures directed to lowering the level of activity were not undertaken) generally do not actively undergo further physiological processes associated with maturation and/or ripening. Rather, the plants/plant products enter a quiescent or suspended state with respect to maturation. The plants/plant products may be referred to as arrested or suspended in an immature or pre-maturation state in which the normal or natural maturation pathway is blocked. Characteristics of such a state include but are not limited to: the plants/plant products do not produce ethylene or produce ethylene at a rate that is less than about 1-5 µl per kilogram plant products per hour (Song and Bangerth, 1996; Obando et al., 2007; Hoffman and Yang, 1980) respiration rates are low (e.g. $CO_2$ is be produced at a rate that is below about 1-15 ml per kilogram plant products per hour (Song and Bangerth, 1996; Ergun et al., 2005; Bower et al., 2002); for fruit, the BRIX score is less than about 5-15 Brix°

(Trought and Bramley, 2011; Raffo et al., 2011; Sinha et al., 2012; Panarese et al., 2012) also for fruit, the level of firmness at or above about 5-15 lbf. (Palafox-Carlos et al., 2012; Sugar and Einhorn, 2011). In addition, blockage may be detected by measuring the level of gene activity, e.g. by measuring AOX mRNA levels, protein levels and/or by measuring the amount or activity of the AOX enzyme, either directly or indirectly.

According to this method, the plants/plant products are released from this quiescent state by human intervention that induces AOX activity, also in an artificial, non-natural occurring manner, generally by exposure to an agent that activates AOX. By "induce AOX activity", we mean that one or more activities attributable to or characteristic of one or more AOX enzymes is induced, effected, increased, augmented, promoted, allowed or caused to proceed, released from inhibition, etc. For example, the ethylene production may occur or increase; respiration rates may increase; sugars may be released; changes in pigment may occur; firmness levels may decrease, etc.

In some aspects, the increase in AOX activity is the result of indirect activation (or reactivation) by turning on or increasing a level of AOX gene expression. Many agents can be used to activate (or reactivate) AOX gene expression. Exemplary agents include but are not limited to: hydrogen sulfide (Xiao et al., 2010); salicylic acid (Rhoads and McIntosh, 1992); pyruvate; hydroxypyruvate; glyoxylate; alanine plus 2-oxoglutarate (Pastore et al., 2001); acetylene (e.g. by application of purified calcium carbide), etc.

In other aspects, an increase in AOX activity is caused directly by activating the enzyme itself, e.g. via generation of a reducing environment (reduction of disulfide bonds within the AOX protein) with a suitable agent such as hydrogen sulfide similar to the methods described in U.S. Pat. Nos. 5,328,839 and 5,652,132 (the complete contents of each of which are herein incorporated by reference) (also as European Patent EP0462674 A1), Umbach et al. (1994) and Perry et al. (1988). Activity of the AOX protein in vivo is thought to be dependent upon its oxidation-reduction state, with activity reported when protein subunits are reduced (Millenaar and Lambers, 2003; Umbach and Siedow, 1993). As a reducing agent, and potent inhibitor of cytochrome c oxidase, hydrogen sulfide (Millenaar and Lambers, 2003) may act in two ways to selectively partition electrons away from the terminus of the electron transport chain (ATP-synthase), and into the alternative oxidase pathway. The presence of α-ketoacids similarly stimulates AOX activity, such as those stated for use in this patent (Millenaar and Lambers, 2003), of which pyruvate, hydroxypyruvate are naturally produced in plant mitochondria at the site of the AOX protein.

The invention provides methods in which AOX activity is intentionally prevented, stopped or lessened at a desired time or point in maturation of a plants/plant material, and then the effects of this action are subsequently reversed at a later date (time) by intentionally exposing the plant/plant material to conditions and/or an agent that activates AOX in order to restart the maturation process. However, the invention also provides methods which involve only the former step or only the latter step are carried out. For example, the plants/plant products may not have been harvested and may not have yet undergone a "natural" ripening process in the field, orchard, etc., and it may be desirable to accelerate maturation on the tree or in the field by increasing AOX activity. This feature of the invention may be especially useful, for example, if different portions or sectors of a crop are ripening or expected to ripen at different rates, and if it would be desirable to hasten the process in the sector(s) that is/are slower so that the entire crop is at the same stage of readiness for harvest at the same time. Alternatively, AOX may be inactivated but only in discrete sectors of a crop which would otherwise mature sooner or earlier than desired, in order to allow other sectors to "catch up". Thus, the invention enables synchronization of production (e.g. maturation, harvest, etc.) of e.g. fruits, vegetables, and other plants. In addition, ripening may also be accelerated as need be to avoid crop loss, e.g. due to an impending, predicted weather untoward weather condition (e.g. low temperatures, frost, flooding, violent storms such as hurricanes, excessive precipitation [e.g. rain], etc.).

Other variants of the methods described herein may also be practiced. For example, one or both of the two steps of inactivation and activation of AOX may be used as necessary to coordinate, as desired, the stage(s) or level(s) of maturity of a crop. For example, maturation or the degree of maturation may be accelerated and/or slowed as needed so as to cause various sectors of a crop to ripen at different times, or to ripen at the same time, e.g. to accommodate the availability of harvesting equipment or personnel, or shipping or market conditions or constraints, or for fruit processing where fruit of equal maturity is desirable, etc. Activation can, for example, speed up ripening and senescence during pre-harvest stages.

The methods of the invention may be applied to any type of plant or plant material (e.g. fruit, vegetables, ornamental plants, etc.) for which it is desirable to control maturation. Thus, the terms "plant and plant material" as used herein are intended to be interpreted broadly, and to include plant-based agricultural products that are typically referred to as fruits, vegetables, grasses, grains, ornamental plants, bulbs, nuts, plant organs, seeds, etc.

With respect to fruit, those of skill in the art will recognize that the word "fruit" may have a variety of meanings. For example, standard definitions include: 1.edible part of plant: an edible part of a plant, usually fleshy and containing seeds; 2. ovary of a plant: the ripened seed-bearing ovary of a plant; and 3. produce: the produce of any plant grown or harvested by humans. In broad terms, "fruit" may refer to a structure of a plant that contains its seeds or a stone or pit. In non-technical usage, such as food preparation, "fruit" may refer to the fleshy seed-associated structures of certain plants that are sweet and edible in the raw state, such as apples, oranges, grapes, strawberries, juniper berries, bananas, etc., although non-sweet or less sweet fleshy structures (e.g. root vegetables such as carrots, beets, sweet potatoes, yams, etc.) are also included. Seed-associated structures that do not fit these informal criteria may be referred to by other names, such as vegetables, pods, ears, etc. In the botany of flowering plants, a "fruit" is a part that derives from specific tissues of the flower, mainly one or more ovaries. Taken strictly, this definition excludes many structures that are "fruits" in the common sense of the term, while including many structures that are not commonly called "fruits", such as bean or pea pods, corn kernels, tomatoes, etc. all of which are encompassed by the present invention.

Many fruits that, in a botanical sense, are true fruits are actually treated as vegetables in cooking and food preparation, including cucurbits (e.g., squash, pumpkin, gourds, melons, cucumbers, etc.), tomatoes, peas, beans, corn, eggplant, and sweet pepper, as wells as some spices, such as allspice and chilies.

As used herein, the term "fruit" refers to all plant products encompassed by the botanical, culinary and common meanings of the word.

Exemplary types of fleshy, simple fruits encompassed by the invention include but are not limited to: stone fruit or drupe (e.g. plum, cherry, peach, apricot, olive, mango, etc.); pome fruits of the family Rosaceae, (including apples, pears, rosehips, saskatoon berry, etc.); aggregate fruits such as achenes (e.g. strawberry), follicles, drupelets (raspberry and blackberry), and various other berries; multiple fruits such as pineapple, fig, mulberry, osage-orange, breadfruit, hedge apple, etc; citrus fruits such as oranges, lemons limes, grapefruits, kumquats, tangelos, ugli fruit, tangerines, tangelos, minnolas, etc.; so-called "true" berries such as black current, red current, gooseberry, tomato, eggplant, guava, lucuma, chilis, pomegranates, kiwi fruit, grape, cranberry, blueberry, etc.; including both seeded and seedless varieties, as well as hybrid and genetically altered or manipulated varieties; and others such a avocados, persimmons, etc.

In one embodiment of the invention, the fruit that is treated using the methods and compositions of the invention is a pear. By "pear" we mean the fruit of a member of the genus *Pyrus*, examples of which include but are not limited to: *Pyrus amygdaliformis* (Almond-leafed pear); *Pyrus armeniacifolia; Pyrus boissieriana; Pyrus bourgaeana* (Iberian pear); *Pyrus×bretschneideri* (Chinese white pear; also classified as a subspecies of *Pyrus pyrifolia*); *Pyrus calleryana* (Callery pear); *Pyrus communis* (European pear); *Pyrus communis* subsp. *communis* (European pear cultivars of which include Beurre d'Anjou, Bartlett and Beurre Bosc); *Pyrus communis* subsp. *caucasica* (syn. *P. caucasica*); *Pyrus communis* subsp. *pyraster* (wild European pear (syn. *Pyrus pyraster*); *Pyrus cordata* (Plymouth pear); *Pyrus cossonii* (Algerian pear); *Pyrus dimorphophylla; Pyrus elaeagnifolia* (oleaster-leafed pear); *Pyrus fauriei; Pyrus gharbiana; Pyrus glabra; Pyrus hondoensis; Pyrus koehnei* (evergreen pear of southern China and Taiwan); *Pyrus korshinskyi; Pyrus mamorensis; Pyrus nivalis* (snow pear); *Pyrus pashia* (Afghan pear); *Pyrus×phaeocarpa; Pyrus pseudopashia; Pyrus pyrifolia* (Nashi pear, Sha Li); *Pyrus regelii; Pyrus salicifolia* (willow-leafed pear); *Pyrus×serrulate, Pyrus× sinkiangensis* (thought to be an interspecific hybrid between *P.×bretschneideri* and *Pyrus communis*); *Pyrus syriaca; Pyrus ussuriensis* (Siberian pear) and *Pyrus xerophila*.

Major types of pears which are marketed and which may be treated by the methods and compositions of the invention include but are not limited to: Williams' Bon Chrétien (sold in the United States. as Bartlett), Red Bartlett varieties, d'Anjou, Bosc, Comice, Concorde, and Seckel pears.

The methods of the invention may also be used to control the development, ripening, maturation or onset or progression of senescence of vegetables. As used herein, the term "vegetable" refers to an edible plant or part of a plant, and typically means the leaf, stem, or root of a plant but also includes some "fruits" as well (such as squash, see above). The meaning of this word is largely based on culinary and cultural tradition and all common meanings that are recognized by those of skill in the art are encompassed herein. Vegetables may be categorized as allium (e.g. onions, garlics, chives, leeks, etc.); *brassica* or cruciferous (e.g. cauliflower, cabbage, cress, bok choy, broccoli, mustards, mustard flowers, cauliflower, turnip, Chinese cabbage, rapeseed, radish, horseradish, arugula (rocket), Daikon radish, maca, Virginia pepperweed, wasabi, watercress etc.); composite (e.g. artichoke, chamomile, chicory, dandelion, endive, Jerusalem artichoke, lettuce, romaine, safflower, salsify, sunflower, etc.); gourds (e.g. cantaloupe, cucumber, melons, pumpkin, squash, watermelon, zucchini, etc.); umbelliferous (e.g. caraway, carrot, celery, cilantro, cumin, dill, fennel, parsley, parsnip, etc.); amaranth/goosefoot (e.g. amaranth, beet, chard, lamb's-quarters, quinoa, spinach, sugar beet, etc.); grass (e.g. bamboo shoots, sweet corn, wheatgrass, sugar cane, etc.); morning glory (e.g. sweet potato, etc.); the yam family; nightshade (e.g. bell or sweet pepper, Italian pepper, chile pepper, eggplant, potato, tomato, tomatillo, and many spices, etc.); legumes (e.g. alfalfa, beans, carob, chickpea, green beans, jicama, lentil, pea, peanut, soy, etc.); mallow (e.g. cacao, cotton, okra, etc.); buckwheat family (e.g. buckwheat, garden sorrel, rhubarb, etc.); and others. Some vegetables are commonly referred to as "root" or "leafy green" vegetables, etc. All such vegetables may be treated using the methods and compositions of the invention.

The methods of the invention may also be used to control the development, maturation or senescence of ornamental plants and hence to preserve their freshness. As used herein, the phrase "ornamental plants" refers to plants that are grown for decorative purposes such as e.g., house plants, those grown for cut flowers, etc. as well as certain grasses, annuals, perennials, shrubs, trees, etc. As used herein the phrase has the same meaning that it is generally used in the horticultural trades.

Other facets of the invention include methods which advantageously exhibit a dual function in that some agents that block AOX activity or that induce AOX activity also have sterilizing properties. Thus, the invention also encompasses methods of simultaneously i) hastening maturation of a plant or plant product and ii) sterilizing the surface of the plant or plant product. The methods comprise a step of applying to a surface of the plant or plant product an agent that i) activates (or inactivates) Alternative Oxidase (AOX) activity and ii) possesses antimicrobial properties.

Application of the agents utilized in the methods may be carried out by any suitable means. Exemplary types of application include but are not limited to: gaseous application such as by fogging; application of a liquid, e.g. by drenching, dipping, spraying, etc. The agent may be in any form suitable for the selected method of application, e.g. as a solution, a solid (e.g. flakes, powder, etc.), in an emulsified form, in a chemically or physically encapsulated form etc. Further, the agents that control AOX activity may be applied alone, or in combination with each other, e.g. two or more agents may be combined. In addition, they may be applied with or without one or more other agents such as but not limited to: penetrants or adjuvants; or agents with other activities such as antimicrobials antifungals, coating materials (e.g. waxes, oils, etc.); antidessicants, etc. Further, delivery may be instantaneous (e.g. all at once during a single application), or by a slow release mechanism e.g. via slow release of a gas during storage in a closed chamber, or by a slow drip mechanism, etc. In addition, single applications may be repeated as necessary to achieve a desired effect, e.g. once per day or every few days for a designated period of weeks or months; or once per week for a designated period of weeks or months; or without a defined schedule as needed.

The agents utilized in the disclosed methods may be applied in any concentration suitable to achieve the desired effect. For example, the agents applied to activate at least one AOX gene, hastens maturation or ripening, or otherwise overcomes blockage in ripening of a fruit can be applied in any concentration to achieve the activation and/or ripening. Ripening can be evidenced, for example, by AOX expression levels or measurable function, evolution of ethylene, fruit softening, increased brix values, and other known measures of ripening. Maturation and/or ripening can be evident within as little as a day, such as 1, 2, 3, 4, 5, 6, 7, 8, 9, 10, 15, 20, or more days from exposure to the agent applied to activate AOX expression or function, and/or otherwise mature ripening. The effect of ripening as determined can be transient, or more preferably, can be long lasting such as maintaining a difference with untreated fruit over the course of several days or even weeks.

In one illustrative embodiment, after a fruit (e.g., pear) has been exposed to an agent to arrest maturation, including but not limited to 1-MCP, the fruit or fruit part is exposed to glyoxylic acid to result in a maturation of the fruit. The glyoxylic acid agent can be applied in any appropriate mode, such as by gaseous application or liquid application (e.g., immersion) at amounts appropriate for the mode of application and sufficient to induce the maturation and/or ripening process. The glyoxylic acid can be applied at a suitable concentration based on the mode of application including but not limited to 0.25 mM, 0.5 mM, 0.75 mM, 1.0 mM, 1.5 mM, 2.0 mM, 2.5 mM, 3.0 mM, 4.0 mM, 5.0 mM, 7.5 mM, 10 mM, 25 mM, 50 mM, 75 mM, 100 mM, 125 mM, 150 mM, 175 mM, 200 mM, 225 mM, 250 mM, 275 mM, 300 mM, 325 mM, 350 mM, 375 mM, 400 mM, or more, glyoxylic acid, or any value contained therein.

In one embodiment, glyoxylic acid agent can be used at a concentration of less than 5.0 mM, or less than 4.0 mM, or less than 3.0 mM, or less than 2.0 mM, or less than 1.0 mM, or less than 0.5 mM.

Figure 6B:
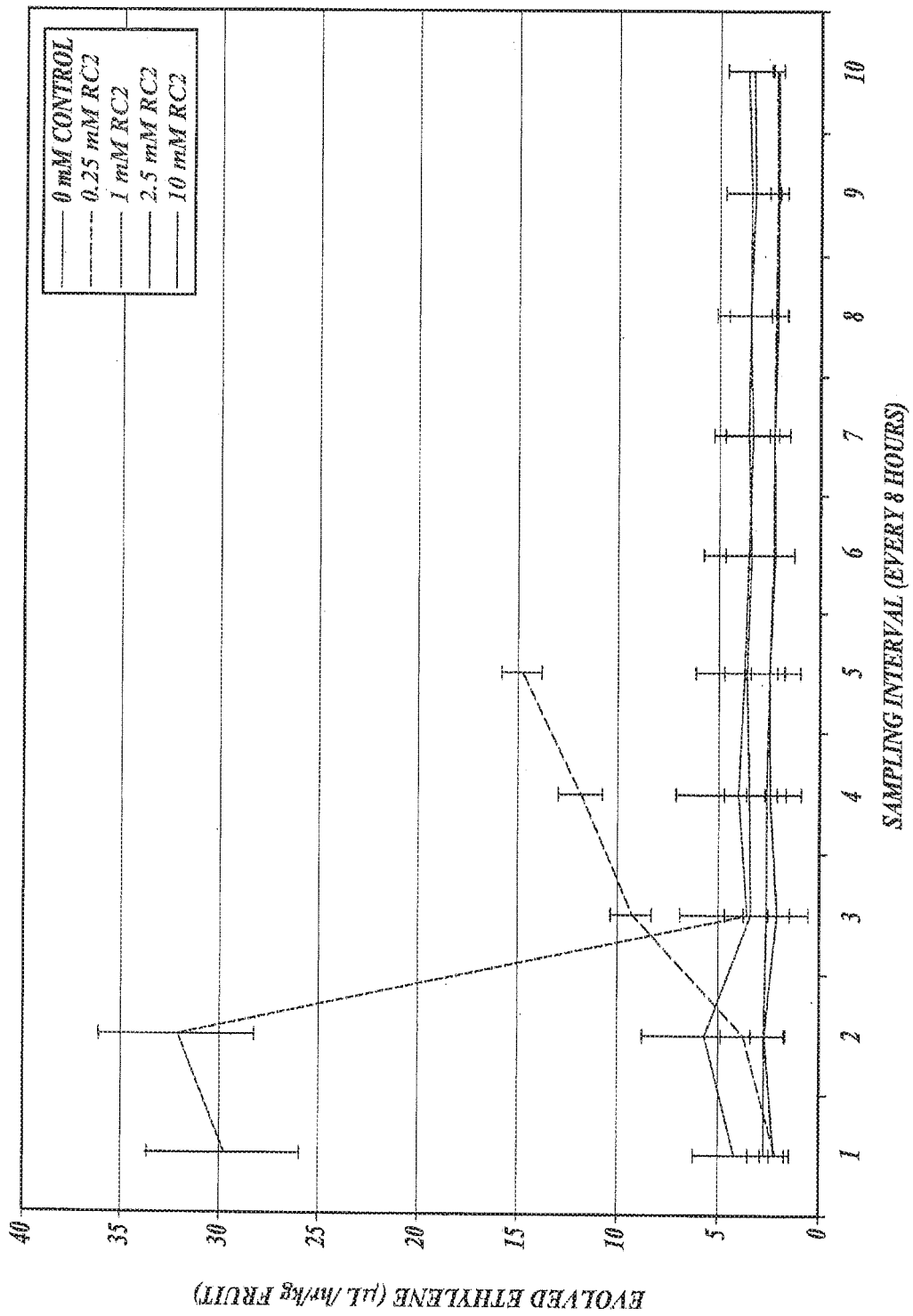

As described in more detail below, it is demonstrated in a series of assays that as little as 0.25 mM glyoxylic acid induces maturation in pears after 1-MCP treatment (see also FIG. 6B). In additional experiments, ethylene and other indicators of ripening were assayed under different exposure conditions to glyoxylic acid, demonstrating that, for example, exposure to 2.5% (337 mM) solution of glyoxylic acid resulted in significantly increased ethylene production by pear slices (see FIG. 11B) and that pears exposed with up to 3% (405 mM) solution of glyoxylic acid resulted in pears that were rated higher in a taste test than pears without glyoxylic acid exposure.

In one illustrative embodiment, after a fruit has been exposed to an agent to arrest maturation, including but not limited to 1-MCP, the fruit or fruit part is exposed to salicylic acid to result in a maturation of the fruit. The salicylic acid agent can be applied in any appropriate mode, such as by gaseous application or liquid application (e.g., immersion) at amounts appropriate for the mode of application and sufficient to induce the maturation and/or ripening process. The salicylic acid can be applied at a suitable concentration based on the mode of application including but not limited to 0.25 mM, 0.5 mM, 0.75 mM, 1.0 mM, 1.5 mM, 2.0 mM, 2.5 mM, 3.0 mM, 4.0 mM, 5.0 mM, 7.5 mM, 10 mM, 25 mM, 50 mM, 75 mM, 100 mM, 125 mM, 150 mM, 175 mM, 200 mM, 225 mM, 250 mM, 275 mM, 300 mM, 325 mM, 350 mM, 375 mM, 400 mM, or more, salicylic acid, or any value contained therein.

In one embodiment, salicylic acid agent can be used at a concentration of less than 5.0 mM, or less than 4.0 mM, or less than 3.0 mM, or less than 2.0 mM, or less than 1.0 mM, or less than 0.5 mM.

In one illustrative embodiment, after a fruit has been exposed to an agent to arrest maturation, including but not limited to 1-MCP, the fruit or fruit part is exposed to pyruvate to result in a maturation of the fruit. The pyruvate agent can be applied in any appropriate mode, such as by gaseous application or liquid application (e.g., immersion) at amounts appropriate for the mode of application and sufficient to induce the maturation and/or ripening process. The pyruvate can be applied at a suitable concentration based on the mode of application including but not limited to 0.25 mM, 0.5 mM, 0.75 mM, 1.0 mM, 1.5 mM, 2.0 mM, 2.5 mM, 3.0 mM, 4.0 mM, 5.0 mM, 7.5 mM, 10 mM, 25 mM, 50 mM, 75 mM, 100 mM, 125 mM, 150 mM, 175 mM, 200 mM, 225 mM, 250 mM, 275 mM, 300 mM, 325 mM, 350 mM, 375 mM, 400 mM, or more, pyruvate, or any value contained therein.

In one embodiment, pyruvate agent can be used at a concentration of less than 5.0 mM, or less than 4.0 mM, or less than 3.0 mM, or less than 2.0 mM, or less than 1.0 mM, or less than 0.5 mM.

In one illustrative embodiment, after a fruit has been exposed to an agent to arrest maturation, including but not limited to 1-MCP, the fruit or fruit part is exposed to hydroxypyruvate to result in a maturation of the fruit. The hydroxypyruvate agent can be applied in any appropriate mode, such as by gaseous application or liquid application (e.g., immersion) at amounts appropriate for the mode of application and sufficient to induce the maturation and/or ripening process. The hydroxypyruvate can be applied at a suitable concentration based on the mode of application to activate at least one AOX gene including but not limited to 0.25 mM, 0.5 mM, 0.75 mM, 1.0 mM, 1.5 mM, 2.0 mM, 2.5 mM, 3.0 mM, 4.0 mM, 5.0 mM, 7.5 mM, 10 mM, 25 mM, 50 mM, 75 mM, 100 mM, 125 mM, 150 mM, 175 mM, 200 mM, 225 mM, 250 mM, 275 mM, 300 mM, 325 mM, 350 mM, 375 mM, 400 mM, or more, hydroxypyruvate, or any value contained therein.

In one embodiment, hydroxypyruvate agent can be used at a concentration of less than 5.0 mM, or less than 4.0 mM, or less than 3.0 mM, or less than 2.0 mM, or less than 1.0 mM, or less than 0.5 mM.

In one illustrative embodiment, after a fruit has been exposed to an agent to arrest maturation, including but not limited to 1-MCP, the fruit or fruit part is exposed to a mixture of alanine and 2-oxoglutarate to result in a maturation of the fruit. The mixture of alanine and 2-oxoglutarate agent can be applied in any appropriate mode, such as by gaseous application or liquid application (e.g., immersion) at amounts appropriate for the mode of application and sufficient to induce the maturation and/or ripening process. The mixture of alanine and 2-oxoglutarate can be applied at a suitable concentration based on the mode of application to activate at least one AOX gene including but not limited to 0.25 mM, 0.5 mM, 0.75 mM, 1.0 mM, 1.5 mM, 2.0 mM, 2.5 mM, 3.0 mM, 4.0 mM, 5.0 mM, 7.5 mM, 10 mM, 25 mM, 50 mM, 75 mM, 100 mM, 125 mM, 150 mM, 175 mM, 200 mM, 225 mM, 250 mM, 275 mM, 300 mM, 325 mM, 350 mM, 375 mM, 400 mM, or more, a mixture of alanine and 2-oxoglutarate, or any value contained therein.

In one embodiment, a mixture of alanine and 2-oxoglutarate can be used at a concentration of less than 5.0 mM, or less than 4.0 mM, or less than 3.0 mM, or less than 2.0 mM, or less than 1.0 mM, or less than 0.5 mM.

In one illustrative embodiment, after a fruit has been exposed to an agent to arrest maturation, including but not limited to 1-MCP, the fruit or fruit part is exposed to a composition comprising two or more of the following agents: hydrogen sulfide, glyoxylic acid, salicylic acid, pyruvate, hydroxypyruvate, or a mixture of alanine and 2-oxoglutarate. The composition can be applied in any appropriate mode, such as by gaseous application or liquid application (e.g., immersion) at amounts appropriate for the mode of application and sufficient to induce the maturation and/or ripening process. The composition can be applied at a suitable concentration based on the mode of application including but not limited to 0.25 mM, 0.5 mM, 0.75 mM, 1.0 mM, 1.5 mM, 2.0 mM, 2.5 mM, 3.0 mM, 4.0 mM, 5.0 mM, 7.5 mM, 10 mM, 25 mM, 50 mM, 75 mM, 100 mM, 125 mM, 150 mM, 175 mM, 200 mM, 225 mM, 250 mM, 275 mM, 300 mM, 325 mM, 350 mM, 375 mM, 400 mM, or more, or any value contained therein.

In one embodiment, the composition can be used at a concentration of less than 5.0 mM, or less than 4.0 mM, or less than 3.0 mM, or less than 2.0 mM, or less than 1.0 mM, or less than 0.5 mM.

In one embodiment, the composition comprises at least the agents hydrogen sulfide and glyoxylic acid.

In one embodiment, the composition comprises at least the agents hydrogen sulfide and salicylic acid.

In one embodiment, the composition comprises at least the agents hydrogen sulfide and pyruvate.

In one embodiment, the composition comprises at least the agents hydrogen sulfide and hydroxypyruvate.

In one embodiment, the composition comprises at least the agents hydrogen sulfide and a mixture of alanine and 2-oxoglutarate.

In one embodiment, the composition comprises at least the agents glyoxylic acid and salicylic acid, In one embodiment, the composition comprises at least the agents glyoxylic acid and pyruvate.

In one embodiment, the composition comprises a least the agents glyoxylic acid and hydroxypyruvate.

In one embodiment, the composition comprises at least the agents glyoxylic acid and a mixture of alanine and 2-oxoglutarate.

In one embodiment, the composition comprises at least the agents salicylic acid and pyruvate.

In one embodiment, the composition comprises at least the agents salicylic acid and hydroxypyruvate.

In one embodiment, the composition comprises at least the agents salicylic acid and a mixture of alanine and 2-oxoglutarate.

In one embodiment, the composition comprises at least the agents pyruvate and hydroxypyruvate.

In one embodiment, the composition comprises at least the agents pyruvate and a mixture of alanine and 2-oxoglutarate.

In one embodiment, the composition comprises at least the agents hydroxypyruvate and a mixture of alanine and 2-oxoglutarate.

The time of exposure to said agent or agents can be adjusted for the intended effect considering the concentration and mode of administration of the agent, according to routine optimization. For example, the agent, e.g., glyoxylic acid, can induce the intended effect of triggering ripening (by various indicators) with an exposure of about 2 hours to about 24 hours or more, such as about 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 hours or more. Plants/plant products treated according to the methods described herein are generally intended for consumption or use by humans. However, plants/plant products intended for consumption or use by animals are also encompassed. In some embodiments, the invention provides a plant/plant product that is treated by one or more of the methods described herein.

The following examples illustrate various embodiments of the invention but should not be interpreted so as to limit the invention in any way.

While illustrative embodiments have been illustrated and described, it will be appreciated that various changes can be made therein without departing from the spirit and scope of the invention.

EXAMPLES

Example 1

As described for the first time herein, work in exemplary produce (pears) which were subjected to cold treatment to induce competency for ripening, has demonstrated that PcAOX1 and 2 (*Pyrus communis* Alternative Oxidase) expression correlates with the stage when 100% physiological competency for ripening is obtained.

Analysis of PcAOX1 and 2 gene expression in ripening Bartlett pears compared to cold-conditioned pears was carried out by reverse transcription quantitative PCR. The results are presented in FIG. 1. As can be seen, both PcAOX1 and PcAOX2 gene expression is activated 3.5 to 3.75-fold in ripening pears over the reference pears.

Bartlett pears were treated with i) 300 ppb of 1-MCP (Smartfresh) and ii) 0.5 and 2.5 mM $H_2S$ solution (RC-1), and iii) glyoxylic acid (RC-2) for 24 hours. Thereafter, each experimental group of fruit was placed in a separate air-tight chamber connected to a gas chromatography (GC) instrument configured to draw samples every 8 hours over the course of 5 days, to measure ethylene via a flame ionizing detector (FID), and to measure $CO_2$ via a gas analyzer. The experiment was performed with 4 pears per chamber in 3 replicates per experimental group. Monitoring was performed to detect minor variation in air flow rates in all experimental chambers used and detected variations were accounted for in subsequent calculations.

After 5 days of monitoring the fruit for ethylene and $CO_2$, fruit were sampled for flesh firmness and soluble solid content, measured in pounds of flesh firmness (lbf) and degrees Brix (respectively). The data were plotted and standard deviations were calculated.

Results

Figure 2:
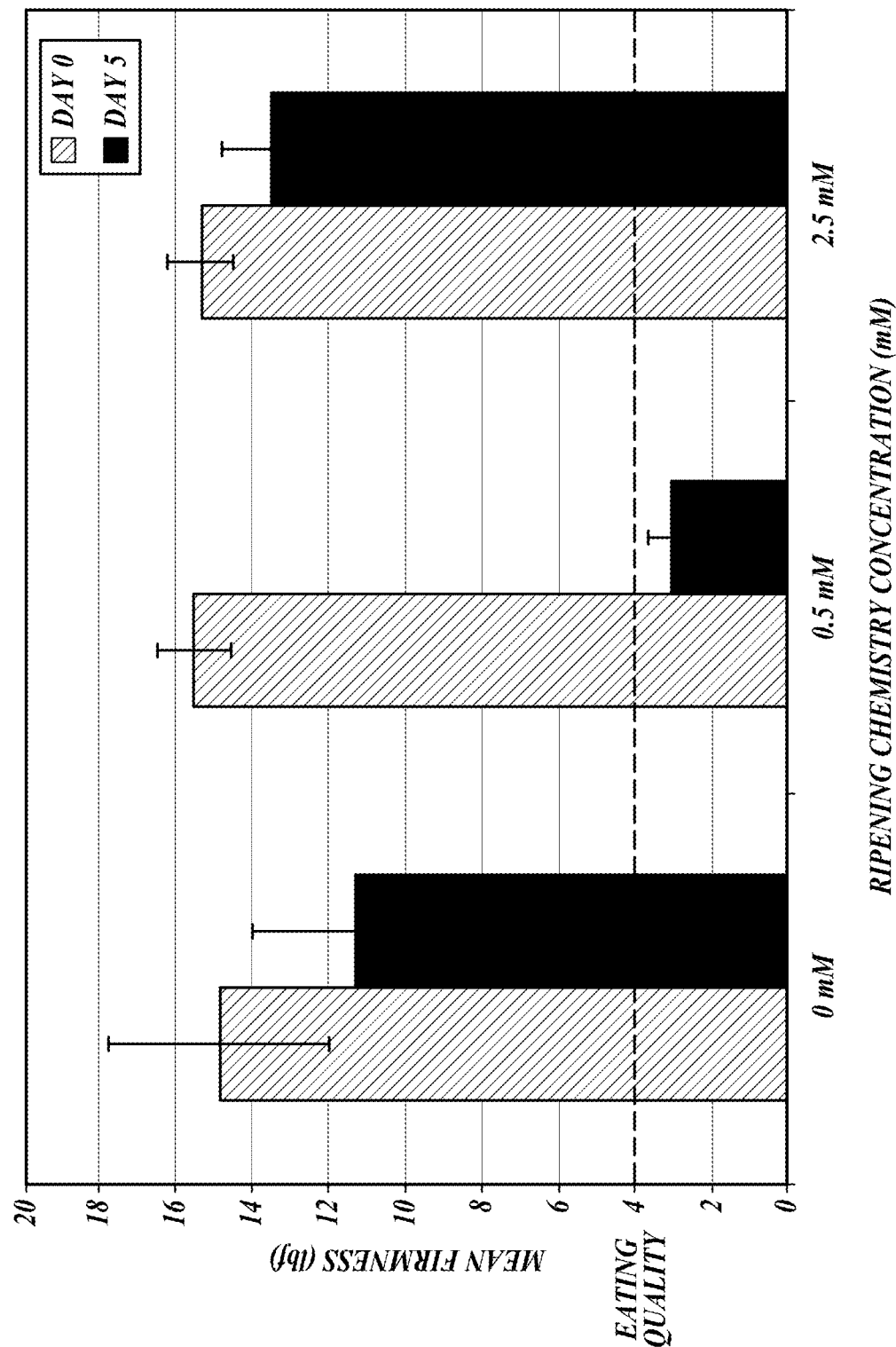
FIG. 2. Mean fruit firmness as calculated on day 0 and day 5. Note the drop in fruit firmness in fruit treated with 0.5 mM of Ripening compound-1 (RC-1) (dark bars). The firmness of 4 lbf and below represents eating quality in pear fruit.
Figure 3:
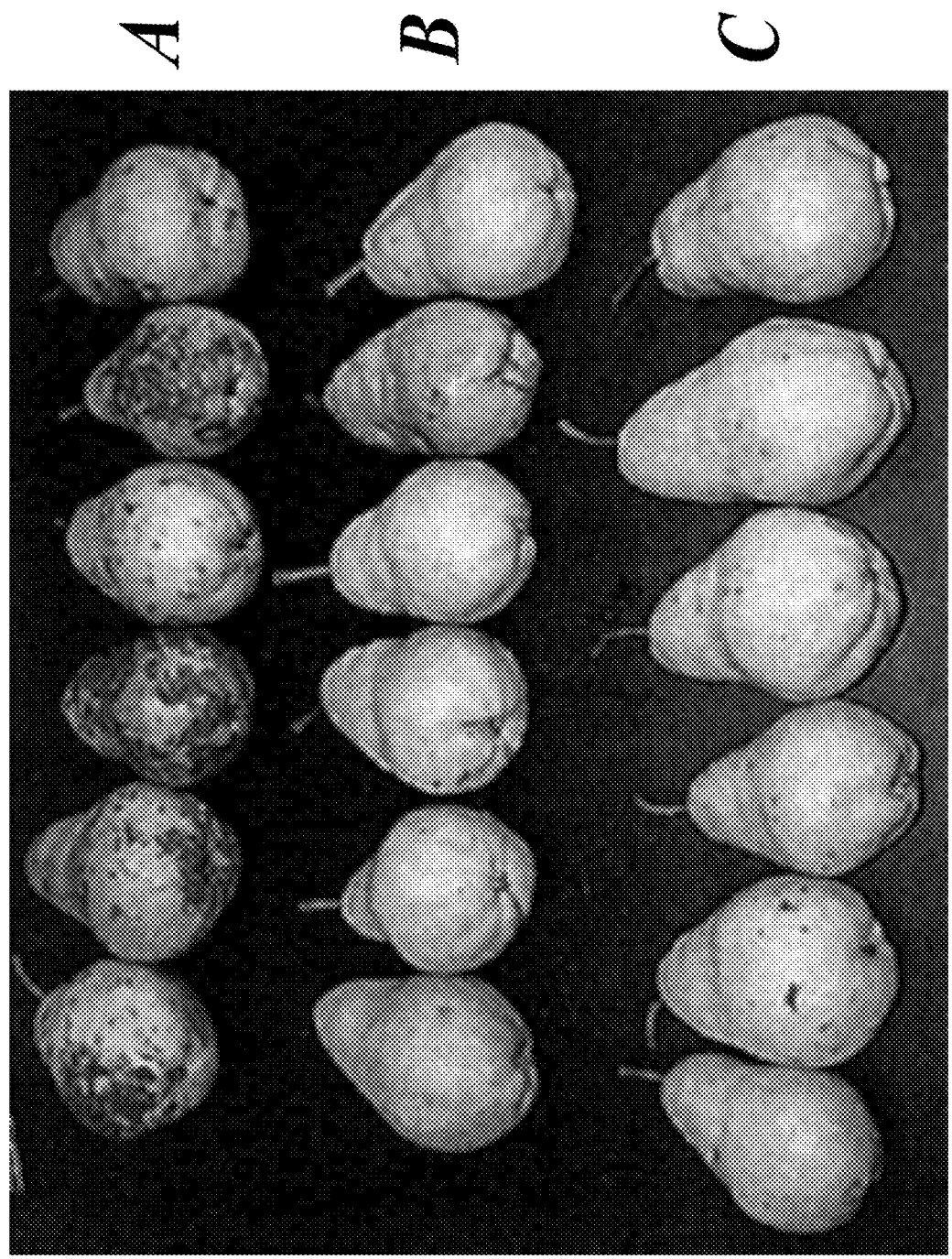
FIG. 3. Bartlett fruit treated with different concentrations of RC-1. Fruit treated with 0.5 mM of RC-1 (C) exhibited a loss of green pigment compared to controls (B).

Firmness: Eating quality in pear fruit correlates to 4 lbf fruit firmness. Compared to control fruit, firmness of fruit treated with 0.5 mM of $H_2S$ (RC-1) dropped to 3.5 lbf (FIG. 2). In addition, it was noted that the $H_2S$-treated fruit lost its green pigmentation (FIG. 3). Interestingly, the higher dosage of $H_2S$ (2.5 mM) was ineffective and resulted in tissue damage.

Figure 4:
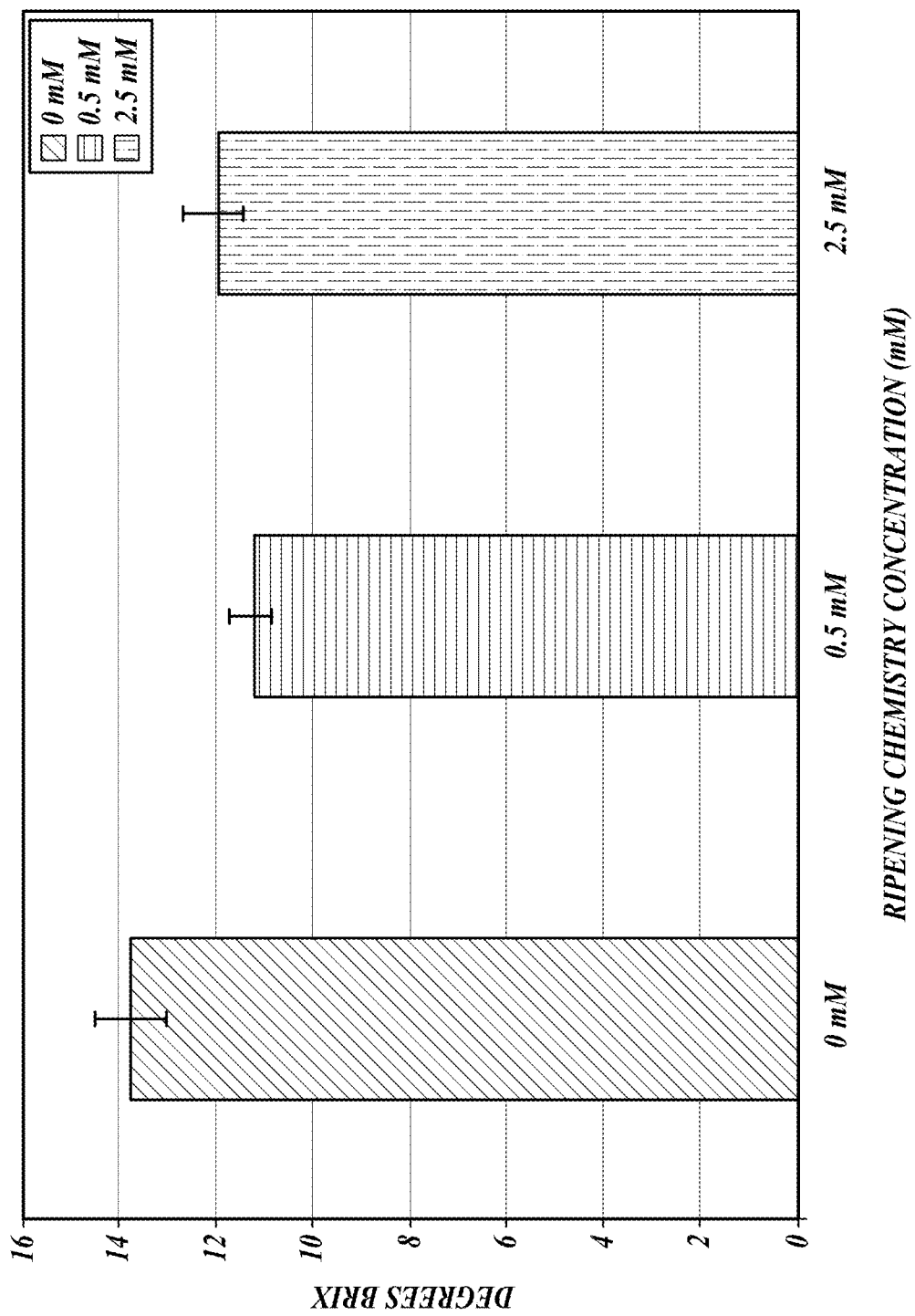
FIG. 4. Change in total soluble solids in fruit treated with RC-1.

Brix score: In the treated fruit, the Brix level, which is an indicator of fruit soluble solids, matched the range of desirable levels in commercial fruit (FIG. 4).

Figure 5:
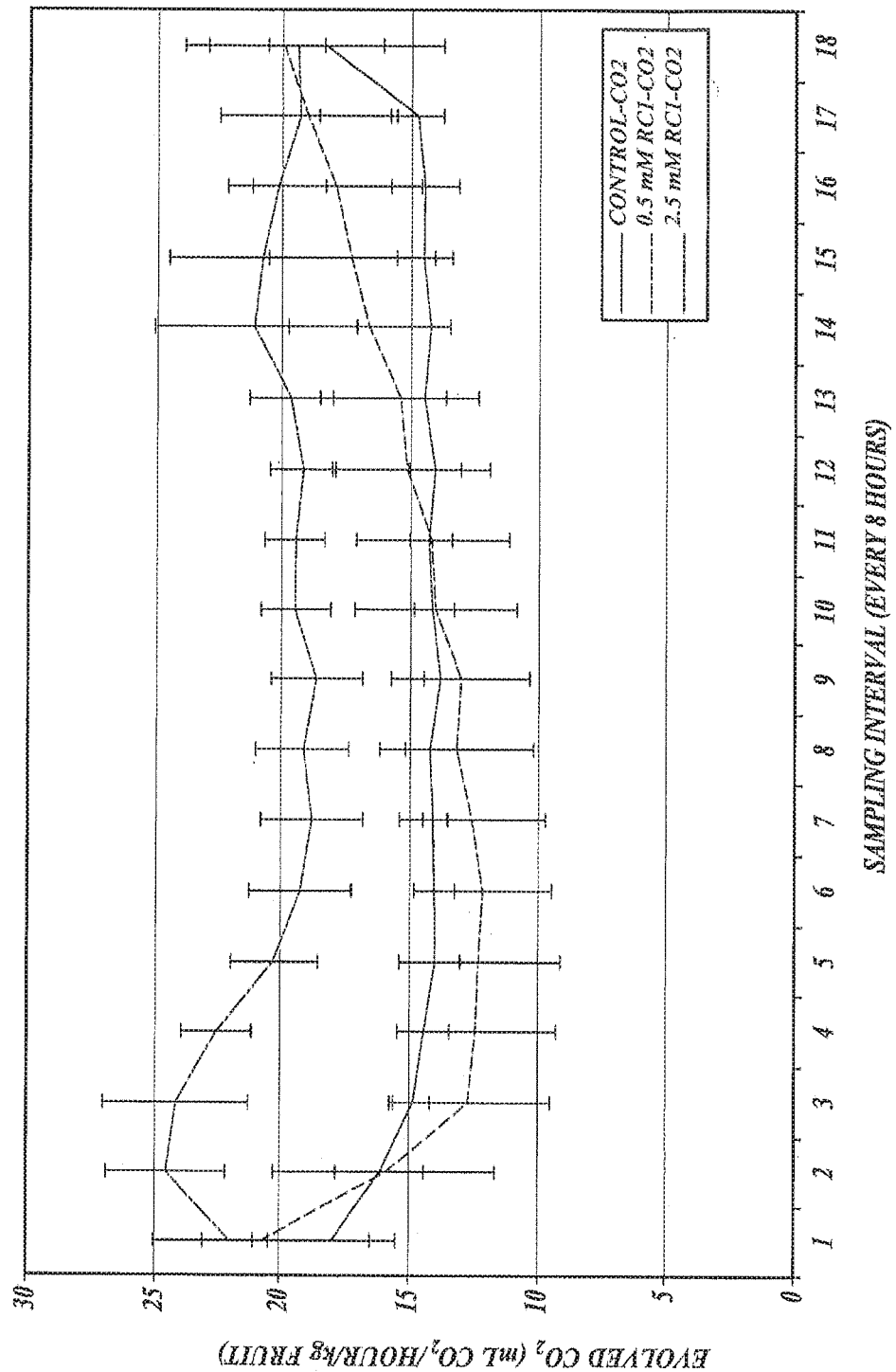
FIG. 5. Evolved $CO_2$ measured in ml per hour per kilogram of fruit. Note the positive trend in fruit treated with 0.5 mM of RC-1.

Carbon dioxide: The level of respiration (as indicated by $CO_2$ levels) in pears treated with 0.5 mM $H_2S$ showed a generally positive trend (FIG. 5) ultimately surpassing the levels observed in fruit treated with 2.5 mM $H_2S$, which showed higher levels of carbon dioxide, perhaps as a stress response. This stress manifests itself in damaged tissues that are visible in FIG. 4. In untreated fruit, the levels of $CO_2$ remained constant.

Ethylene: The most important characteristic of fruit during climacteric or ripening is release of ethylene. Ethylene production was measured as microliters of ethylene per hour per kilogram of fruit. The level of ethylene in the control fruit and fruit treated with 2.5 mM of $H_2S$ (FIG. 6A) or with 1, 2.5 and 10 mM of glyoxylic acid (FIG. 6B) remained indistinguishable and very low. However, in the fruit treated with 0.5 mM of $H_2S$ and 0.25 mM glyoxylic acid (RC-2), a clear and steady increase in the evolution of ethylene was observed (FIGS. 6A and B), correlating well with the decrease in fruit firmness and concomitant change in the amount of total soluble solids, and demonstrating the effectiveness of this approach to the induction of ripening.

Example 2

Introduction: The above example demonstrated that ripening could be restarted after treatment of 1-MCP with exposure to concentrations of ripening compounds (RC) $H_2S$ (RC-1) or glyoxylic acid (RC-2) at various concentrations. The present example describes additional studies to further characterize the effect of glyoxylic acid exposure on fruit that have had the ripening inhibited by 1-MCP. Several factors such as mode of exposure, concentration of exposure, timing of effect, and state of fruit (i.e., whole or sliced), were tested. The results discussed below illustrate that application of various concentrations of glyoxylic acid can re-initiate the ripening process in whole or sliced pear. The Ripening of 1-MCP Pre-Treated Whole Pears with Glyoxylic Acid In order to ripen whole pear fruit pretreated with 1-MCP, the fruits were treated by immersion in 0 mM, 0.1 mM, 0.25 mM, 0.5 mM glyoxylic acid. In other experiments, the fruits were treated by ambient fogging of fruit with 1 liter of solution of 1% (0.135 M), 2% (0.270 M) and 3% (0.405 M) glyoxylic acid solution (determined with 74 as the molecular weight of glyoxylic acid). The ambient fogging was carried out in a 192,000 $cm^3$ volume chamber using an ultrasonic humidifier. Various indicators of ripening were assayed thereafter.

Figure 7:
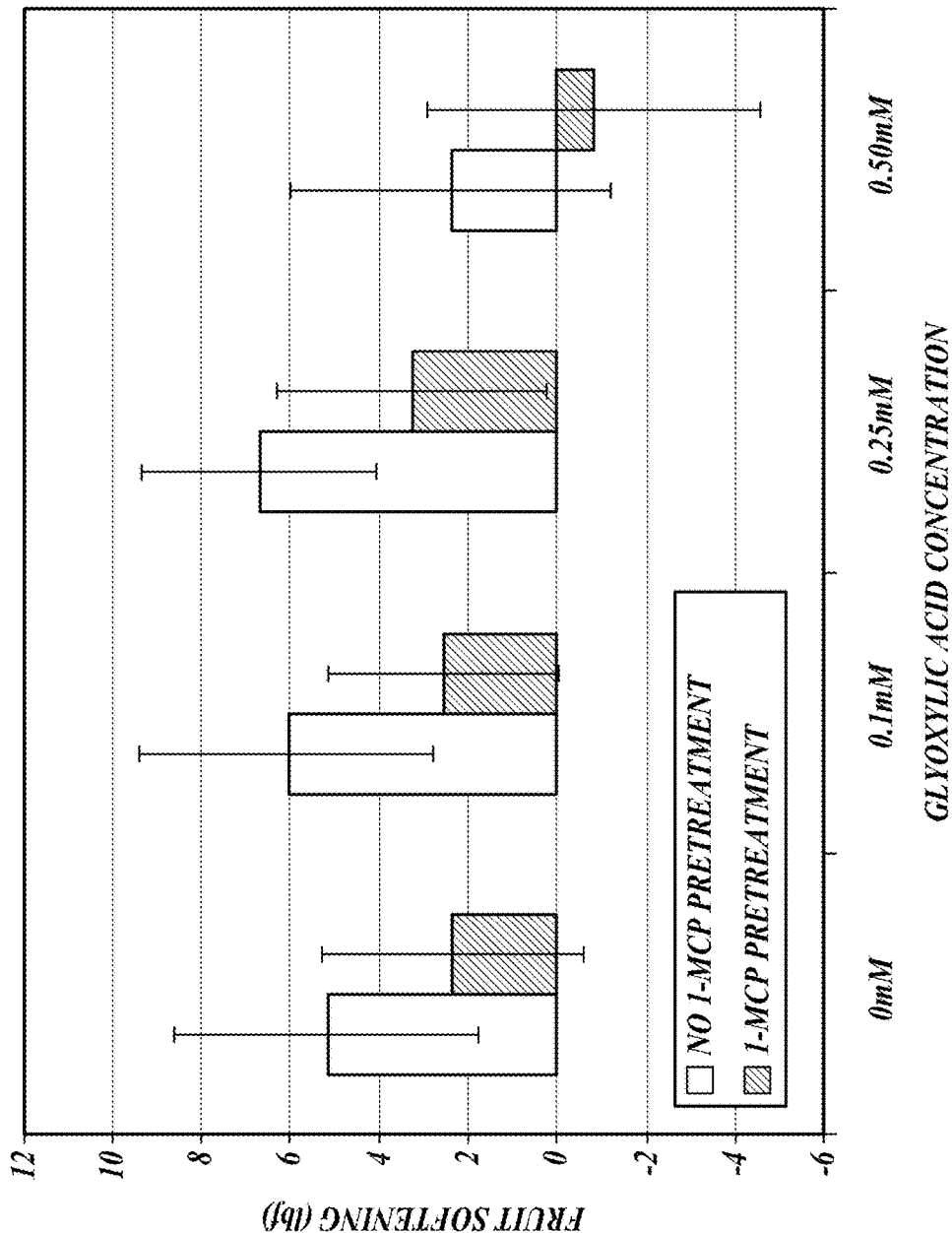
FIG. 7. Reduction in firmness (i.e., development of softness) in pear fruit treated with various concentrations of glyoxylic acid. Whole fruit was immersed in glyoxylic acid solution for 24 hours. Firmness was measured after 6 days of the immersion treatment. Light gray bars represent fruit firmness data from non-1-MCP treated fruit and dark bars represent fruit firmness from 1-MCP treated fruit.

In a first assay, whole pears pre-treated with 1-MCP were immersed in 0 mM, 0.1 mM, 0.25 mM, or 0.5 mM glyoxylic acid solution for 24 hours. The fruit was assayed for firmness using a penetrometer six days after the immersion treatment. FIG. 7 graphically illustrates the reduction in firmness (i.e., development of softness) in pear fruit treated with various concentrations of glyoxylic acid. Non-1-MCP treated fruit (light bars) and 1-MCP treated fruit (dark bars) responded differently to glyoxylic acid treatment. As illustrated, after 6 days, glyoxylic acid immersion results in a drop in firmness in 1-MCP treated fruit at all concentrations of glyoxylic acid when compared to the non-1-MCP treated fruit. The effect is especially enhanced over control for immersion in the 0.5 mM immersion solution. In the non-1-MCP treated fruit also the reduction in firmness is evident at the 0.5 mM concentration.

Figure 8:
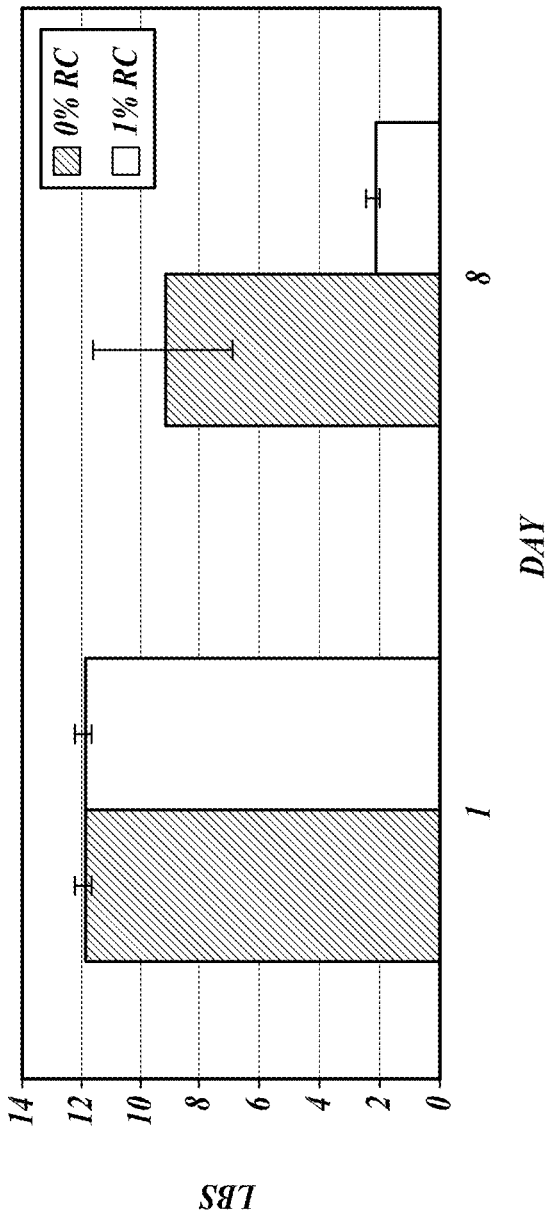
FIG. 8. Firmness of 1-MCP pre-treated fruit treated with 0% or 1% glyoxylic acid using ambient fogging. Dark bars represent the 1-MCP fruit treated with 0% glyoxylic acid. Light bars represent the 1-MCP fruit treated with 1% glyoxylic acid.
Figure 9:
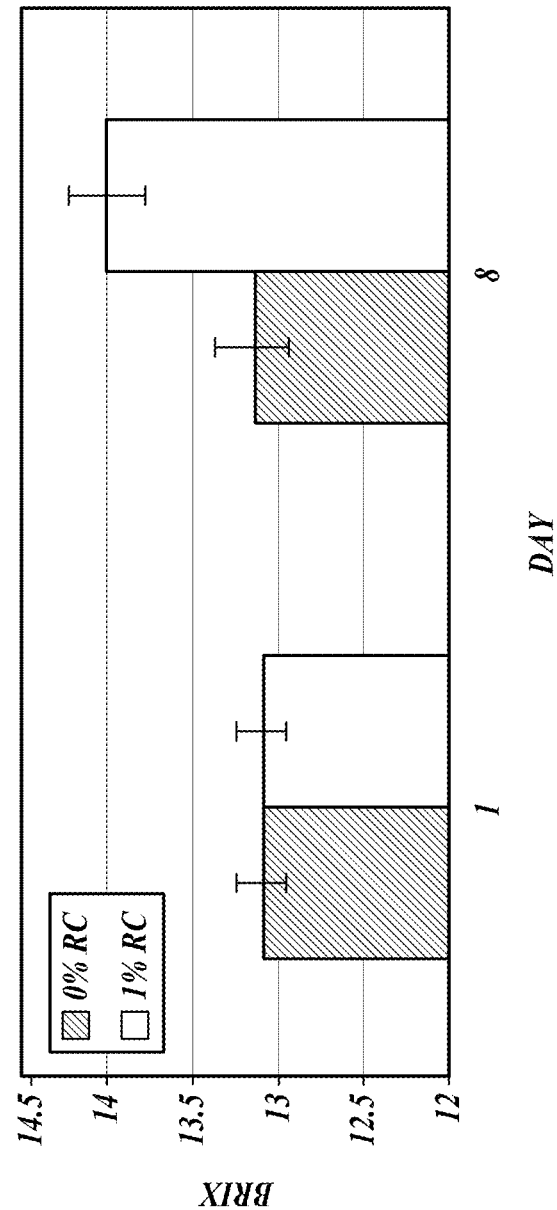
FIG. 9. Brix percentage representing total soluble solids in 1-MCP treated fruit treated with 0% or 1% glyoxylic acid using ambient fogging. Dark bars represent the 1-MCP fruit treated with 0% glyoxylic acid. Light bars represent the 1-MCP fruit treated with 1% glyoxylic acid.

Next, 1-MCP pre-treated fruit were treated with glyoxylic acid using ambient fogging at 0% or 1% (0.135 M) glyoxylic acid. In this experiment, the fruit firmness was measured at two time points—immediately after the fogging treatment and again 8 days later using a penetrometer. As illustrated in FIG. 8, the fruit treated with 1% (0.135 M) glyoxylic acid ambient fogging softened to 2 lbf fruit firmness in 8 days indicating proper ripening. In sharp contrast, the 1-MCP treated control with 0% glyoxylic acid fogging did not have any significant change in firmness. The fruit were also assessed for ripeness by assaying the Brix values, which are indicative of total soluble solids and also serve as an industry standard for fruit ripening. As illustrated in FIG. 9, fruit treated with 1% (0.135 M) glyoxylic acid ambient fogging exhibited significantly increased ripening (i.e., significantly increased brix values) at 8 days post fogging treatment, whereas the brix of the 1-MCP treated control fruit did not change after the passage of 8 days from control fogging. All these experiments have been repeated multiple times and have been consistent with the above data.

Ripening of 1-MCP Pre-Treated Fruit with Glyoxylic Acid after Slicing

The effect of glyoxylic acid on the restarting of ripening after 1-MCP-mediated arrest was also assayed with fruit that was sliced. Whole unripe pears were pre-treated with 1-MCP according to standard practice. The unripe pre-treated fruit were sliced and subject to glyoxylic acid treatments to assess its ability to induce ripening in the sliced fruit. First, fruit slices were immersed in 0.5 mM and 2.5 mM glyoxylic acid solution for 12-24 hours and placed in an airtight jar. Ethylene levels were measured after 8 hours. As illustrated in FIG. 10, the fruit slices immersed in the 0.5 mM glyoxylic acid solution generated 5-fold more ethylene than the control slices. Slices immersed in the 2.5 mM glyoxylic also produced more (approximately 2-fold more) ethylene than the controls, although the increase in ethylene levels was not as high as for the 0.5 mM treatment.

Figure 11A:
Figure 14B:
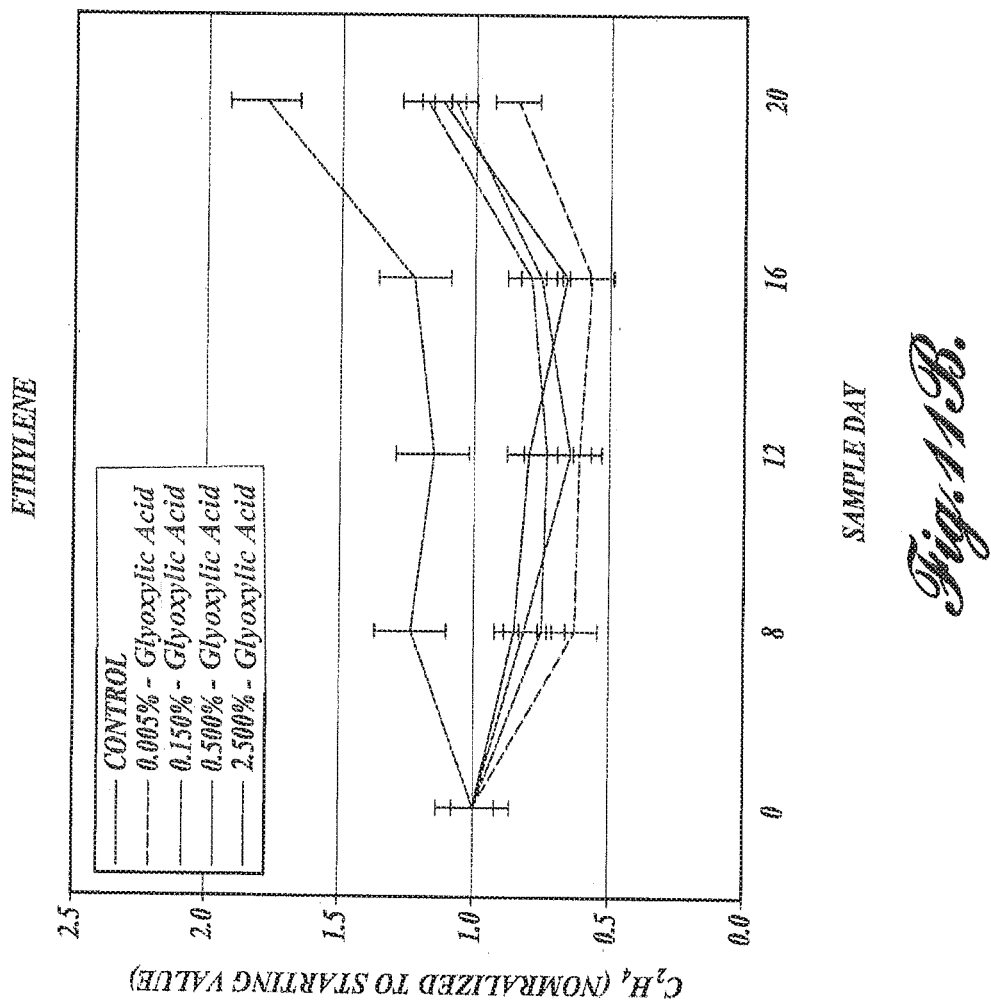

Next, a modified protocol was followed to expose fruit slices derived from 1-MCP pre-treated fruit to solutions of glyoxylic acid. Glyoxylic acid solutions ranging from 0.005% (0.675 mM), 0.150% (20.25 mM), 0.5% (0.6.75 mM), 1% (0.135 M), 2% (0.270 M), 2.5% (0.338 M) and 3% (0.405 M) were prepared either alone or in conjunction with the Nature seal solution, which contains antioxidants that prevent fruit oxidation. 1-MCP fruit was sliced and treated with the 0.005%, 0.150%, 0.5% or 2.5% glyoxylic acid solutions and placed in a modified, sealed atmosphere bag. See FIG. 11A. The amount of evolved ethylene was measured directly from the sealed bag of fruit. As illustrated in FIG. 11B, the presence of glyoxylic acid, especially at 2.5%, in a sealed atmospheric bag enhanced the evolution of ethylene from sliced fruit compared to the control sliced fruit.

Finally, the 1-MCP fruit that were sliced and treated with 1%, 2% and 3% glyoxylic acid were evaluated in consumer preference trials in 2014 and 2015. In both years, 1-MCP fruit when sliced and treated with glyoxylic acid was generally preferred over controls, especially for factors of taste/flavor and texture, due to the fact that the glyoxylic acid fruit had ripened (Table 1).

TABLE 1

Results of the consumer preference trials. Note that in both years, consumers found 1-MCP pre-treated fruit, when sliced and treated with glyoxylic acid, was most acceptable. The number of respondents in both years was 40.

|  | Overall acceptance | Appearance | Taste/Flavor | Texture |
|---|---|---|---|---|
| Ranking 2014 | | | | |
| Most acceptable | 2% RC | Control | 2% RC | 3% RC |
| ↓ | Control | 1% RC | 3% RC | 2% RC |
| ↓ | 3% RC | 2% RC | Control | Control |
| Least acceptable | 1% RC | 3% RC | 1% RC | 1% RC |
| Ranking 2015 - Anjou | | | | |
| Most acceptable | 3% RC | 1% RC | 3% RC | 3% RC |
| ↓ | 2% RC | Control | 2% RC | 2% RC |
| ↓ | Control | 2% RC | 1% RC | 1% RC |
| Least acceptable | 1% RC | 3% RC | Control | Control |

Another large scale consumer trial was performed in 2016 with 122 consumers. The 2016 trial also found that the 1-MCP pre-treated fruit subsequently exposed to glyoxylic acid (RC) was most preferable over the controls that did not receive a subsequent glyoxylic acid treatment (Table 2).

TABLE 2

Overall liking, number (percentage) of panelists who rated each sample as mostly preferred, second most preferred, third most preferred and least preferred.

| | Number of panelists who rated the sample as | | | |
|---|---|---|---|---|
| | 1 (most preferred) | 2 | 3 | 4 (least preferred) |
| 0% RC | 23 (19%) | 28 (23%) | 32 (27%) | 38 (31%) |
| 1% RC | 22 (18%) | 30 (24%) | 36 (30%) | 33 (28%) |
| 2% RC | 42 (35%) | 23 (19%) | 29 (24%) | 27 (22%) |
| 3% RC | 34 (28%) | 39 (32%) | 24 (20%) | 24 (20%) |
| Total number of panelists | 121 (100%) | 121 (100%) | 121 (100%) | 122 (100%) |

Note:
Numbers in parenthesis indicate percentages.

As an additional confirmation of glyoxylic acid-mediated ripening of 1-MCP pre-treated pears, the internal ethylene of the fruit was also measured. First, the whole fruit with or without 1-MCP pre-treatment were treated with 0.5% (0.6.75 mM) or 1% (0.135 M) glyoxylic acid using ambient fogging. Thereafter, one quarter of four separate pears from each treatment was sliced into four pieces and placed into a gas extraction chamber. A vacuum was created using an aspirator. For each experiment, 0.5 ml of extracted ethylene gas was injected into the GC/MS in three replicates. Measurements of ethylene in ppm were calculated using a previously established standard curve. As illustrated in FIG. 12, in both 1-MCP pre-treated and non-1-MCP pre-treated fruit, 0.5% and 1% glyoxylic acid were both effective in inducing the evolution of ethylene. It is noteworthy that the 1-MCP pre-treated fruit that was not treated with glyoxylic acid demonstrated no change in ethylene evolution.

These results demonstrate by various measures (firmness, brix, ethylene production, etc.) that glyoxylic acid exposure on whole pear and sliced pear fruit can induce ripeness, even after the ripening process has been inhibited by 1-MCP pre-treatment. The effect was observed whether the glyoxylic acid was administered by immersion in liquid solution or by ambient atmospheric fogging. Accordingly, glyoxylic acid is effective in reversing the effects of 1-MCP, thereby inducing the ripening of fruit or fruit parts (e.g., pear slices).

REFERENCES

Song, J., and Bangerth, F. 1996. The effect of harvest date on aroma compound production from 'Golden Delicious' apple fruit and relationship to respiration and ethylene production. Postharvest Biol. and Technol. 8, 259-269.

Ramina, A., Chang, C., Giovannoni, J., Klee, H., Perata, P., Woltering, E. (eds.), Advances in Plant Ethylene Research: Proceedings of the 7$^{th}$ International Symposium on the Plant Hormone Ethylene, 197-205. 2007. Springer.

Hoffman, N. E., and S. F. Yang. 1980. Changes of 1-aminocyclopropane-1-carboxylic acid content in ripening fruits in relation to their ethylene production rates. J. Am. Soc. Hort. Sci. 105(4):492-495.

Ergun, M., Jeong, J., Huber, D. J., and Cantliffe, D. J. 2005. Suppression of ripening and softening of 'Galia' melons by 1-methylcyclopropene applied at preripe or ripe stages of development. HortSci. 40(1), 170-175.

Bower, J., Holford, P., Latch, A., Pech, J. 2002. Culture conditions and detachment of the fruit influence the effect of ethylene on the climacteric respiration of melon. Postharvest Biol. and Technol. 26(2), 135-146.

Trought, M. C. T., and Bramley, R. G. V. 2011. Vineyard variability in Marlborough, New Zealand: characterising spatial and temporal changes in fruit composition and juice quality in the vineyard. Australian J. Grape and Wine Res. 17(1), 79-89.

Raffo, M. D., Candan, A. P., De Angelis, V., Mañueco, L., Miranda, M. J., and Barda, N. 2011. Sensory evaluation of pears: a useful tool to detect changes in eating quality during ripening. Acta Hort. 909, 651-656.

Sinha, N., Sidhu, J., Barta, J., Wu, J., and Cano, M. P. (eds., Handbook of Fruits and Fruit Processing, 369-375. 2012. John Wiley & Sons.

Panarese, V., Tylewicz, U., Santagapita, P., Rocculi, P., Rosa, M. D. 2012. Isothermal and differential scanning calorimetries to evaluate structural and metabolic alterations of osmo-dehydrated kiwifruit as a function of ripening stage. Innov. Food Sci. and Emerging Technol. 15, 66-71.

Palafox-Carlos, H., Yahia, E., Islas-Osuna, M. A., Gutierrez-Martinez, P., Robles-Sánchez, M., González-Aguilar, G. A. 2012. Effect of ripeness stage of mango fruit (Mangifera indica L., cv. Ataulfo) on physiological parameters and antioxidant activity. Scientia Hortic. 135, 7-13.

Sugar, D., and Einhorn, T. C. 2011. Conditioning temperature and harvest maturity influence induction of ripening capacity in 'd'Anjou' pear fruit. Postharvest Biol. and Technol. 60(2), 121-124.

Duque, P., and Arrabaca, J. D. (1999) Respiratory metabolism during cold storage of apple fruit. II. Alternative oxidase is induced at the climacteric. Physiologia Plantarum, 107(1), 24-31.

Umbach, A. L., Wiskich, J. T., and Siedow, J. N. 1994. Regulation of alternative oxidase kinetics by pyruvate and intermolecular disulfide bond redox status in soybean seedling mitochondria. FEBS Letters. 348(2), 181-184.

Perry, D., Abraham, E. P., and Baldwin, J. E. 1988. Factors affecting the isopenicillin N synthetase reaction. Biochem. J. 255(1), 345-351.

Millenaar, F. F., and Lambers, H. 2003. The Alternative Oxidase: in vivo regulation and function. Plant Biol. 5(1), 2-15.

Umbach, A. L., and Siedow, J. N. 1993. Covalent and noncovalent dimers of the cyanide-resistant alternative oxidase protein in higher plant mitochondria and their relationship to enzyme activity. Plant Physiol. 103, 845-854.

Pastore, D., Trono, D., Laus, M. N., Di Fonzo, N., and Passarella, S. (2001) Alternative oxidase in durum wheat mitochondria. Activation by pyruvate, hydroxypyruvate and glyoxylate and physiological role. Plant and Cell Physiology, 42(12), 1373-1382.

Rhoads, D. M., and Mcintosh, L. (1992) Salicylic-Acid Regulation of Respiration in Higher-Plants—Alternative Oxidase Expression. Plant Cell, 4(9), 1131-1139.

Xiao, M., Ma, J., Li, H. Y., Jin, H., and Feng, H. Q. (2010) Effects of Hydrogen Sulfide on Alternative Pathway Respiration and Induction of Alternative Oxidase Gene Expression in Rice Suspension Cells. Zeitschrift Fur Naturforschung Section C-a Journal of Biosciences, 65(7-8), 463-471.

Xu, F., Yuan, S., Zhang, D. W., Lv, X., and Lin, H. H. (2012) The role of alternative oxidase in tomato fruit ripening and its regulatory interaction with ethylene. J Exp Bot, 63(15), 5705-5716.

All references cited herein, including patents and patent applications, are hereby incorporated by reference in entirety.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

The embodiments of the invention in which an exclusive property or privilege is claimed are defined as follows:

1. A method of storing and subsequently maturing a pear, the method comprising
   exposing said pear to 1-methylcyclopropene (1-MCP) to arrest maturation of said pear; and, subsequently,
   exposing said pear to glyoxylic acid that results in maturation of said pear as evidenced by evolution of ethylene in an amount greater than in the absence of glyoxylic acid.

2. The method of claim 1, wherein glyoxylic acid is applied as a gas or as a liquid.

3. The method of claim 1, wherein glyoxylic is applied by drenching, by spraying, or by a slow release method.

4. The method of claim 1, wherein glyoxylic acid is applied with an antimicrobial agent.

5. The method of claim 1, wherein said step of exposing said pear to 1-methylcyclopropene (1-MCP) is carried out in combination with exposure to cold.

6. The method of claim 1, wherein one or both of said steps of exposing are carried out under pre-harvest conditions.

7. The method of claim 1, wherein one or both of said steps of exposing are carried out under post-harvest conditions.

8. The method of claim 1, wherein said step of exposing to 1-methylcyclopropene (1-MCP) is carried out under pre-harvest conditions and said step of exposing to glyoxylic acid is carried out under post-harvest conditions.

9. The method of claim 1, further comprising a step of cutting or slicing said pear after said first exposing step and before said second exposing step.

10. The method of claim 1, wherein maturation of said pear is evidenced within 8 hours of exposure to the glyoxylic acid by evolution of ethylene in an amount greater than in the absence of glyoxylic acid exposure.

11. A method of overcoming blockage in ripening or senescence of a pear or pear product, the method comprising:
    exposing said pear or pear product that has previously been exposed to 1-methylcyclopropene (1-MCP) to glyoxylic acid that results in maturation of said pear or pear product as evidenced by evolution of ethylene in an amount greater than in the absence of glyoxylic acid.

12. The method of claim 11, wherein glyoxylic acid is applied with an antimicrobial agent.

13. The method of claim 11, wherein said pear or pear product was also previously exposed to cold.

14. The method of claim 11, wherein said step of exposing to said glyoxylic acid is carried out under pre-harvest conditions.

15. The method of claim 11, wherein said step of exposing to glyoxylic acid is carried out under post-harvest conditions.

16. The method of claim 11, further comprising a step of cutting or slicing said pear before exposing to said glyoxylic acid.

* * * * *